United States Patent
Kim et al.

(10) Patent No.: US 10,418,561 B2
(45) Date of Patent: Sep. 17, 2019

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Jung-Keun Kim, Seoul (KR); Do-Han Kim, Goyang-si (KR); Jeong-Dae Seo, Incheon (KR); Ji-Cheol Shin, Seoul (KR); Heung-Woo Choi, Daejeon (KR); Wan-Pyo Hong, Daejeon (KR); Sang-Duk Suh, Daejeon (KR); Joo-Yong Yoon, Daejeon (KR); Sung-Kil Hong, Daejeon (KR)

(73) Assignee: LG DISPLAY CO., LTD., Seoul (KR)

( * ) Notice: Subject to any disclaimer, the term of this patent is extended or adjusted under 35 U.S.C. 154(b) by 196 days.

(21) Appl. No.: 15/684,567

(22) Filed: Aug. 23, 2017

(65) Prior Publication Data
US 2018/0062083 A1   Mar. 1, 2018

(30) Foreign Application Priority Data

Aug. 31, 2016   (KR) .................. 10-2016-0111582

(51) Int. Cl.
*C07D 213/57* (2006.01)
*H01L 51/00* (2006.01)
(Continued)

(52) U.S. Cl.
CPC ........ *H01L 51/0058* (2013.01); *C07C 255/47* (2013.01); *C07D 213/57* (2013.01);
(Continued)

(58) Field of Classification Search
None
See application file for complete search history.

(56) References Cited

U.S. PATENT DOCUMENTS 6,423,429 B2   7/2002   Kido et al.
7,981,324 B2   7/2011   Hartmann et al.
(Continued)

FOREIGN PATENT DOCUMENTS

EP   2833700 A1   2/2015
EP   3026727 A1   6/2016
(Continued)

*Primary Examiner* — Robert S Loewe
(74) *Attorney, Agent, or Firm* — Birch, Stewart, Kolasch & Birch, LLP

(57) ABSTRACT

An embodiment of the present invention provides an organic compound represented by following Formula:

[Formula]

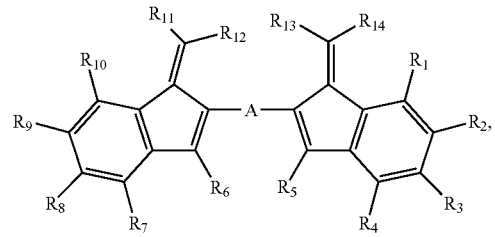

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group (CN), fluorine, tri-fluoro methyl, tri-fluoro methoxy and trimethylsilyl, and at least one of $R_1$ to $R_{10}$ is the cyano group, and wherein at least one of $R_{11}$ to $R_{14}$ is the cyano group, and A is selected from substituted or non-substituted $C_6$ to $C_{30}$ aryl and substituted or non-substituted $C_3$ to $C_{30}$ heteroaryl. The
(Continued)

present invention also provides an organic light emitting diode and an organic light emitting display device including the organic compound.

20 Claims, 3 Drawing Sheets

(51) Int. Cl.
*C07C 255/47* (2006.01)
*H01L 27/32* (2006.01)
*H01L 51/50* (2006.01)
*H01L 51/52* (2006.01)

(52) U.S. Cl.
CPC ...... *H01L 51/0067* (2013.01); *H01L 27/3244* (2013.01); *H01L 51/5004* (2013.01); *H01L 51/5044* (2013.01); *H01L 51/5056* (2013.01); *H01L 51/5088* (2013.01); *H01L 51/5206* (2013.01); *H01L 51/5221* (2013.01); *H01L 51/5278* (2013.01); *H01L 2251/552* (2013.01)

(56) References Cited

U.S. PATENT DOCUMENTS 8,057,712 B2  11/2011  Zeika et al.
8,288,013 B2  10/2012  Morishita

FOREIGN PATENT DOCUMENTS

| | | | | |
|---|---|---|---|---|
| JP | 8-211635 A | | 8/1996 | |
| KR | 10-0622179 B1 | | 9/2006 | |
| KR | 20150076029 | * | 6/2015 | ............ C09K 11/06 |
| KR | 10-2016-0064361 A | | 6/2016 | |

* cited by examiner

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims the priority benefit of Korean Patent Application No. 10-2016-0111582 filed in Republic of Korea on Aug. 31, 2016, which is hereby incorporated by reference into the present application.

BACKGROUND OF THE INVENTION

Field of the Invention

The present invention relates to an organic compound and more particularly to an organic compound being capable of reducing a driving voltage of an organic light emitting diode and improving an emitting efficiency of the organic light emitting diode and the organic light emitting display device including the organic compound.

Discussion of the Related Art

As requests for a flat panel display device having a small occupied area have increased, an organic light emitting display (OLED) device including an organic light emitting diode has been the subject of recent research.

The organic light emitting diode emits light by injecting electrons from a cathode as an electron injection electrode and holes from an anode as a hole injection electrode into an emission compound layer, combining the electrons with the holes, generating an exciton, and transforming the exciton from an excited state to a ground state. A flexible substrate, for example, a plastic substrate, can be used as a base substrate where elements are formed. Since the OLED does not require a backlight assembly, the OLED has low weight and low power consumption. Moreover, the OLED can be operated at a voltage (e.g., 10V or below) lower than a voltage required to operate other display devices.

In the organic light emitting diode, to efficiently inject the hole into an emitting material layer (EML), a hole injection layer (HIL) and a hole transporting layer (HTL) may be formed between the anode and the EML. In this instance, the HIL may include a single material or a matrix with a p-type dopant.

For example, the HAT-CN compound may be used for the single material or the p-type dopant. However, there is problems of high driving voltage and low emitting efficiency in the organic light emitting diode including the HAT-CN compound in the HIL.

SUMMARY OF THE INVENTION

Accordingly, the present invention is directed to an organic compound and an organic light emitting diode and an organic light emitting display (OLED) device including the same that substantially obviate one or more of the problems due to limitations and disadvantages of the related art.

An object of the present invention is to provide an organic compound being capable of preventing problems of high driving voltage and low emitting efficiency.

An object of the present invention is to provide an organic light emitting diode and an OLED device having low driving voltage and high emitting efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is represented by following Formula:

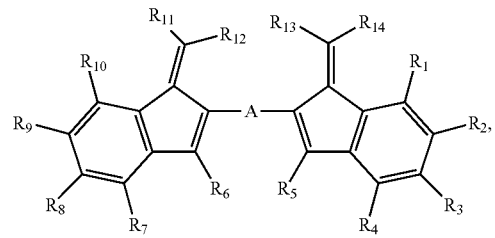

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group (CN), fluorine, tri-fluoro methyl, tri-fluoro methoxy and trimethylsilyl, and at least one of $R_1$ to $R_{10}$ is the cyano group, and wherein at least one of $R_{11}$ to $R_{14}$ is the cyano group, and A is selected from substituted or non-substituted $C_6$ to $C_{30}$ aryl and substituted or non-substituted $C_3$ to $C_{30}$ heteroaryl.

In another aspect, an organic light emitting diode comprises first and second electrodes facing each other; a first emitting part between the first and second electrodes and including a hole injection layer, a first hole transporting layer and a first emitting material layer; and an electron auxiliary layer between the first emitting part and the second electrode, wherein the first hole transporting layer includes an organic compound represented by following Formula:

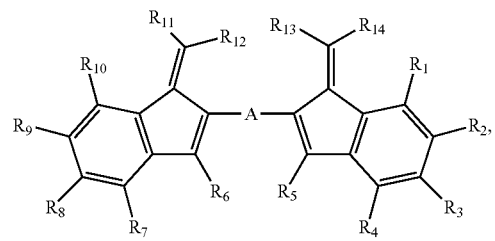

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group (CN), fluorine, tri-fluoro methyl, tri-fluoro methoxy and trimethylsilyl, and at least one of $R_1$ to $R_{10}$ is the cyano group, and wherein at least one of $R_{11}$ to $R_{14}$ is the cyano group, and A is selected from substituted or non-substituted $C_6$ to $C_{30}$ aryl and substituted or non-substituted $C_3$ to $C_{30}$ heteroaryl.

In another aspect, an organic light emitting diode comprises first and second electrodes facing each other; a first emitting part between the first and second electrodes; a second emitting part between the first emitting part and the second electrode and including a hole transporting layer; and a charge generation layer between the first and second emitting parts, wherein the charge generation layer includes an organic compound represented by following Formula:

[Formula]

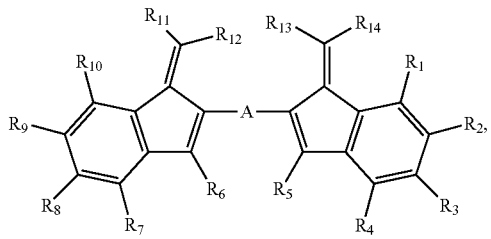

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group (CN), fluorine, tri-fluoro methyl, tri-fluoro methoxy and trimethylsilyl, and at least one of $R_1$ to $R_{10}$ is the cyano group, and wherein at least one of $R_{11}$ to $R_{14}$ is the cyano group, and A is selected from substituted or non-substituted $C_6$ to $C_{30}$ aryl and substituted or non-substituted $C_3$ to $C_{30}$ heteroaryl.

In another aspect, an organic light emitting display device comprises a substrate; an organic light emitting diode over the substrate and including first and second electrodes facing each other, a first emitting part between the first and second electrodes and including a hole injection layer, a first hole transporting layer and a first emitting material layer and an electron auxiliary layer between the first emitting part and the second electrode; and a thin film transistor between the substrate and the organic light emitting diode and connected to the organic light emitting diode, wherein the first hole transporting layer includes an organic compound represented by following Formula:

[Formula]

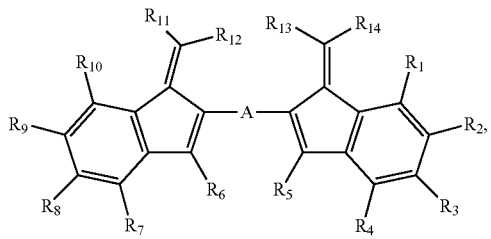

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group (CN), fluorine, tri-fluoro methyl, tri-fluoro methoxy and trimethylsilyl, and at least one of $R_1$ to $R_{10}$ is the cyano group, and wherein at least one of $R_{11}$ to $R_{14}$ is the cyano group, and A is selected from substituted or non-substituted $C_6$ to $C_{30}$ aryl and substituted or non-substituted $C_3$ to $C_{30}$ heteroaryl.

In another aspect, an organic light emitting display device comprises a substrate; an organic light emitting diode over the substrate and including first and second electrodes facing each other, a first emitting part between the first and second electrodes, a second emitting part between the first emitting part and the second electrode and including a hole transporting layer and a charge generation layer between the first and second emitting parts; and a thin film transistor between the substrate and the organic light emitting diode and connected to the organic light emitting diode, wherein the charge generation layer includes an organic compound represented by following Formula:

[Formula]

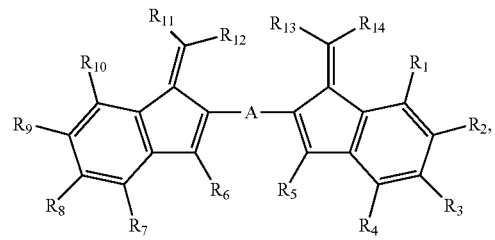

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group (CN), fluorine, tri-fluoro methyl, tri-fluoro methoxy and trimethylsilyl, and at least one of $R_1$ to $R_{10}$ is the cyano group, and wherein at least one of $R_{11}$ to $R_{14}$ is the cyano group, and A is selected from substituted or non-substituted $C_6$ to $C_{30}$ aryl and substituted or non-substituted $C_3$ to $C_{30}$ heteroaryl.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Reference will now be made in detail to the preferred embodiments, examples of which are illustrated in the accompanying drawings.

Figure 1:
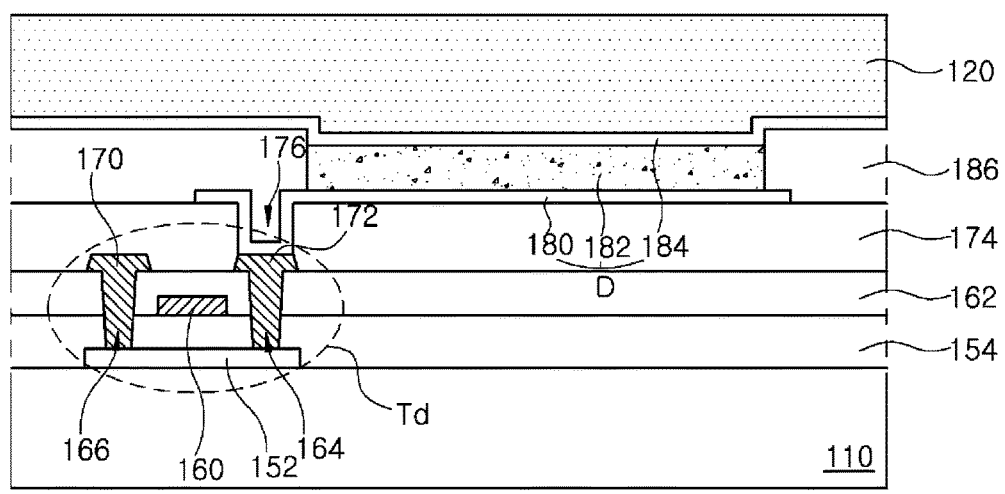
FIG. 1 is a schematic cross-sectional view of an OLED device according to an embodiment of the present invention.

FIG. 1 is a schematic cross-sectional view of an OLED device according to the present invention. All the components of the OLED device according to all embodiments of the present invention are operatively coupled and configured.

As shown in FIG. 1, an OLED device 100 includes a substrate 110, an organic light emitting diode D over the substrate 110, an encapsulation film 120 covering the organic light emitting diode D.

A driving thin film transistor (TFT) Td is disposed on the substrate 110, and the organic light emitting diode D is connected to the driving TFT Td.

Although not shown, a gate line and a data line are disposed on or over the substrate 110 and cross each other to define a pixel region. In addition, a power line, which is parallel to and spaced apart from the gate line or the data line, a switching TFT, which is electrically connected to the gate line and the data line, and a storage capacitor, which is connected to the power line and an electrode of the switching TFT may be formed on or over the substrate 110.

The driving TFT Td is connected to the switching TFT and includes a semiconductor layer 152, a gate electrode 160, a source electrode 170 and a drain electrode 172.

The semiconductor layer 152 is formed on the substrate 110. The semiconductor layer 152 may be formed of an oxide semiconductor material or a poly-silicon.

When the semiconductor layer 152 includes the oxide semiconductor material, a light-shielding pattern (not shown) may be formed under the semiconductor layer 152. The light to the semiconductor layer 152 is shielded or blocked by the light-shielding pattern such that thermal degradation of the semiconductor layer 152 can be prevented. On the other hand, when the semiconductor layer 152 includes polycrystalline silicon, impurities may be doped into both sides of the semiconductor layer 152.

A gate insulating layer 154 is formed on the semiconductor layer 152. The gate insulating layer 154 may be formed of an inorganic insulating material such as silicon oxide or silicon nitride.

The gate electrode 160, which is formed of a conductive material, e.g., metal, is formed on the gate insulating layer 154 to correspond to a center of the semiconductor layer 152. The gate electrode 160 is connected to the switching TFT.

An interlayer insulating layer 162, which is formed of an insulating material, is formed on an entire surface of the substrate 110 including the gate electrode 160. The interlayer insulating layer 162 may be formed of an inorganic insulating material, e.g., silicon oxide or silicon nitride, or an organic insulating material, e.g., benzocyclobutene or photo-acryl.

The interlayer insulating layer 162 includes first and second contact holes 164 and 166 exposing both sides of the semiconductor layer 152. The first and second contact holes 164 and 166 are positioned at both sides of the gate electrode 160 to be spaced apart from the gate electrode 160.

The source electrode 170 and the drain electrode 172, which are formed of a conductive material, e.g., metal, are formed on the interlayer insulating layer 162. The source electrode 170 and the drain electrode 172 are spaced apart from each other with respect to the gate electrode 160 and respectively contact both sides of the semiconductor layer 152 through the first and second contact holes 164 and 166.

In the driving TFT Td, the gate electrode 160, the source electrode 170 and the drain electrode 172 are positioned over the semiconductor layer 150. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

The switching TFT may have substantially the same structure as the driving TFT Td.

A passivation layer 174, which includes a drain contact hole 176 exposing the drain electrode 172 of the driving TFT Td, is formed to cover the driving TFT Td.

A first electrode 180, which is connected to the drain electrode 172 of the driving TFT Td through the drain contact hole 176, is separately formed on the passivation layer 174 in each pixel region.

The first electrode 180 may be an anode and may be formed of a conductive material having a relatively high work function. For example, the first electrode 180 may be formed of a transparent conductive material such as indium-tin-oxide (ITO), indium-zinc-oxide (IZO) or zinc oxide (ZnO).

When the OLED device 100 of the present invention is a top-emission type, a reflection electrode or a reflection layer may be formed under the first electrode 180. For example, the reflection electrode or the reflection layer may be formed of aluminum (Al), silver (Ag), nickel (Ni) or aluminum-palladium-copper (APC) alloy.

A bank layer 186, which covers edges of the first electrode 180, is formed on the passivation layer 174. The bank 186 exposes a center of the first electrode 180 in the pixel region.

An organic emitting layer 182 is formed on the first electrode 180. As explained below, the organic emitting layer 182 may include a single emitting part. Alternatively, the organic emitting layer 182 may include at least two emitting parts such that the organic light emitting diode D has a tandem structure.

A second electrode 184 is formed over the substrate 110 including the emitting layer 182. The second electrode 184 is positioned at an entire surface of the display area. The second electrode 184 may be a cathode and may be formed of a conductive material having a relatively low work function. For example, the second electrode 184 may be formed of aluminum (Al), magnesium (Mg) or Al—Mg alloy.

The first electrode 180, the emitting layer 182 and the second electrode 184 constitute the organic light emitting diode D.

On the other hand, at least two emitting parts with a charge generation layer therebetween may be formed between the first and second electrode 180 and 184 such that a white organic light emitting diode may be provided. In this instance, a color filter layer (not shown) may be formed under or over the organic light emitting diode D.

The encapsulation film 120 is formed on the organic light emitting diode D to prevent penetration of moisture into the organic light emitting diode D. For example, the encapsulation film 120 may has a triple-layered structure of a first inorganic layer, an organic layer and a second inorganic layer. However, it is not limited thereto.

Figure 2:
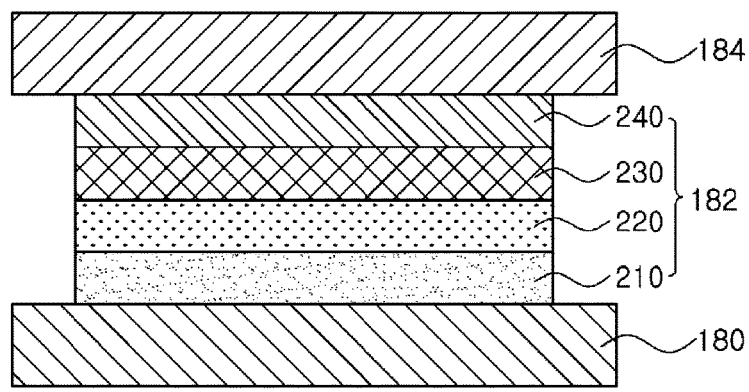
FIG. 2 is a schematic cross-sectional view of an organic light emitting diode according to a first embodiment of the present invention.

FIG. 2 is a schematic cross-sectional view of an organic light emitting diode according to a first embodiment of the present invention.

As shown in FIG. 2, the organic light emitting diode D includes a first electrode 180, a second electrode 184, an organic emitting layer 182 between the first and second electrodes 180 and 184 and including a hole injection layer (HIL) 210, a hole transporting layer (HTL) 220, an emitting material layer (EML) 230 and an electron auxiliary layer 240. Namely, the organic light emitting diode D of the first embodiment of the present invention includes a single emitting part.

As mentioned above, the first electrode 180 is the anode for injecting a hole and includes a high work function conductive material, e.g., ITO, IZO or ZO. The second electrode 184 is the cathode for injecting an electron and includes a low work function conductive material, e.g., Al, Mg or Al—Mg alloy.

The HIL 210 is positioned between the first electrode 180 and the HTL 220, and the HTL 220 is positioned between the HIL 210 and the EML 230. The electron auxiliary layer 240 is positioned between the EML 230 and the second electrode 184. For example, the electron auxiliary layer 240 may include an electron transporting layer (ETL) and an electron injection layer (EIL) sequentially stacked on the EML 230.

The HIL 210 may be a p-type HIL. For example, the HIL 210 may include a host material and a p-type dopant or a single material of the p-type dopant.

The p-type dopant has a strong electron withdrawing substituent. The electron in the HTL 220 or in the host material of the HIL 210 is withdrawn by the p-type dopant such that an electron path (or an electron transporting path) is provided. Namely, the p-type dopant has a strong electron withdrawing property.

To increase the electron withdrawing property, a p-type dopant including a cyano-substituent or a fluorine-substituent, each of which has the strong electron withdrawing property, is introduced.

For example, the F4-TCNQ compound is introduced as the p-type dopant. However, since the F4-TCNQ compound has a relatively small molecular weight, the F4-TCNQ compound has high sublimation property such that there may be problems of the contamination of the deposition source, the reproducibility of the device, the thermal stability of the device, and so on.

On the other hand, the HAT-CN compound of following Formula, which has a relatively high molecular weight, is introduced as the p-type dopant. However, the HAT-CN compound has high lowest unoccupied molecular orbital (LUMO) level such that there may be problems of high driving voltage and low emitting efficiency.

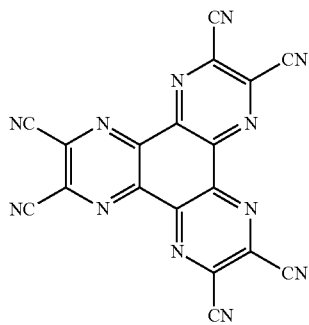 [SMILES: N#Cc1nc2c3nc(C#N)c(C#N)nc3c3nc(C#N)c(C#N)nc3c2nc1C#N]

The electron moves from the highest occupied molecular orbital (HOMO) level of the HTL or the host material of the HIL into the LUMO level of the p-type dopant such that the electron path is generated. Namely, to efficiently generate the electron path, the LUMO level of the p-type dopant and the HOMO level of the HTL or the host material of the EIL should be similar to each other.

However, since the HAT-CN compound has high LUMO level, the increase problem of the driving voltage and the decrease problem of the emitting efficiency are generated in the organic light emitting diode D.

The HIL 210 in the organic light emitting diode D according to the first embodiment of the present invention includes an organic compound in Formula 1. Namely, the HIL 210 includes the organic compound without other compounds or the organic compound as the p-type dopant with a host material. The organic compound may have a weight % of about 1 to 50 with respect to the host material.

[Formula 1]

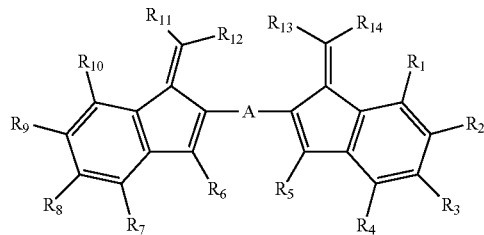

In the Formula 1, each of R1 to R10 may be independently selected from hydrogen, substituted or non-substituted C6 to C12 aryl, substituted or non-substituted C3 to C11 heteroaryl, substituted or non-substituted C1 to C10 alkyl, substituted or non-substituted C1 to C10 alkoxy, ether, cyano group (CN), fluorine, tri-fluoro methyl, tri-fluoro methoxy and trimethylsilyl, and at least one of R1 to R10 is the cyano group.

In addition, each of R11 to R14 may be independently selected from hydrogen, substituted or non-substituted C6 to C12 aryl, substituted or non-substituted C3 to C11 heteroaryl, substituted or non-substituted C1 to C10 alkyl, substituted or non-substituted C1 to C10 alkoxy, ether, cyano group, fluorine, tri-fluoro methyl, tri-fluoro methoxy and trimethylsilyl, and at least one of R11 to R14 is the cyano group. All of R11 to R14 may be the cyano group.

In addition, "A" is selected from substituted or non-substituted C6 to C30 aryl and substituted or non-substituted C3 to C30 heteroaryl. For example, "A" may be one of benzene (phenylene), naphthalene (naphthalenylene), pyridine (pyridinylene), diazine (diazinylene), dibenzofurane (dibenzofuranylene) and dibenzothiophene (dibenzothiophenylene). The substituent of "A" may be selected from fluorine, cyanide, C6 to C12 aryl and C3 to C12 heteroaryl.

The organic compound of the present invention in the Formula 1 has the strong (high) electron withdrawing property and high thermal stability. In addition, the organic compound of the present invention in the Formula 1 has the low LUMO level. For example, the organic compound may have the LUMO level of about −5.8 to −5.4 eV.

Namely, the LUMO level of the organic compound is substantially equal to or less than the HOMO level of the HTL 220 or the host material in the HIL 210. Accordingly, the organic compound of the present invention in the HIL 210 easily receives the electron from the HTL 220 or the host material in the HIL 210 such that the electron path is also easily provided or generated. In other words, the electron transporting efficiency in the organic light emitting diode D, which includes the organic compound of the Formula 1 in the HIL 210, is improved such that the driving voltage is decreased and the emitting efficiency is increased.

For example, the organic compound of the Formula 1 may be one of the materials in Formula 2.
[Formula 2]
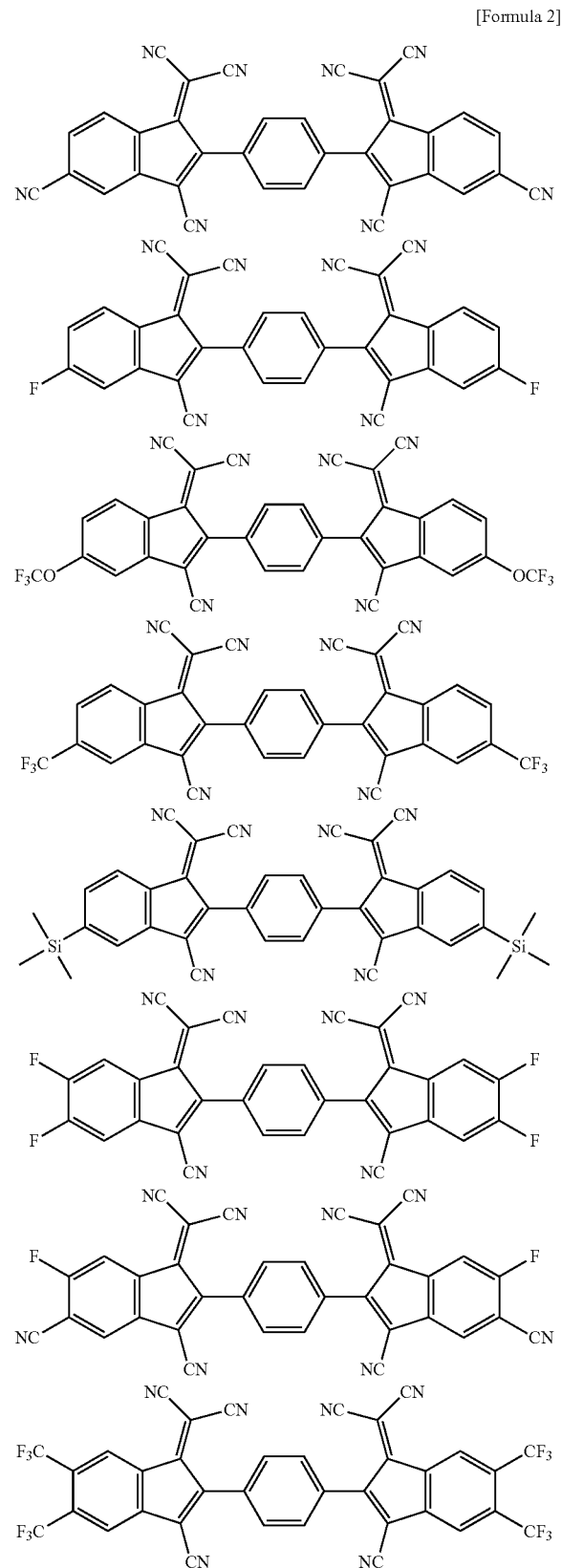
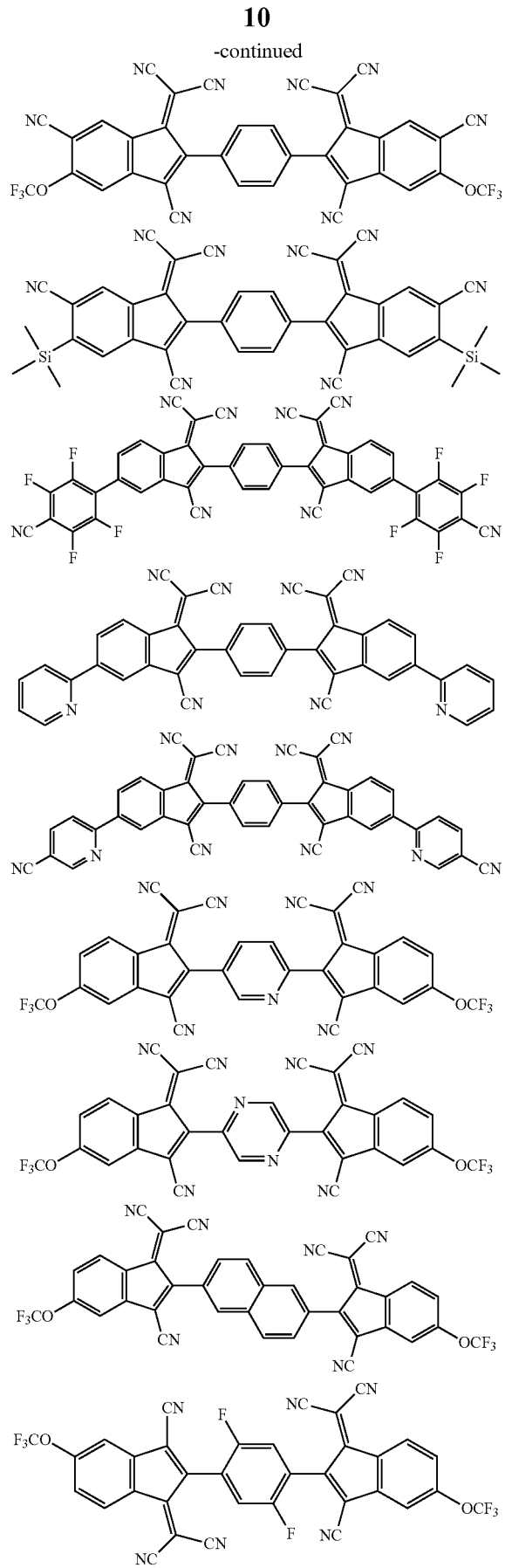

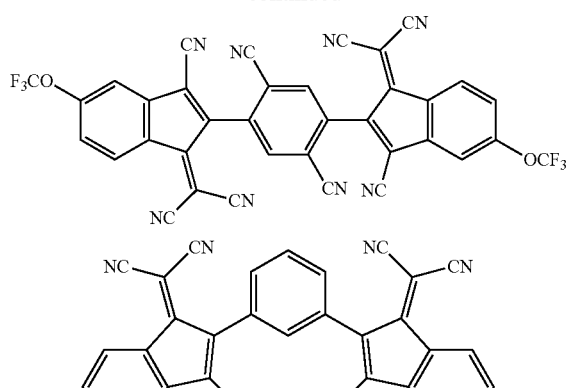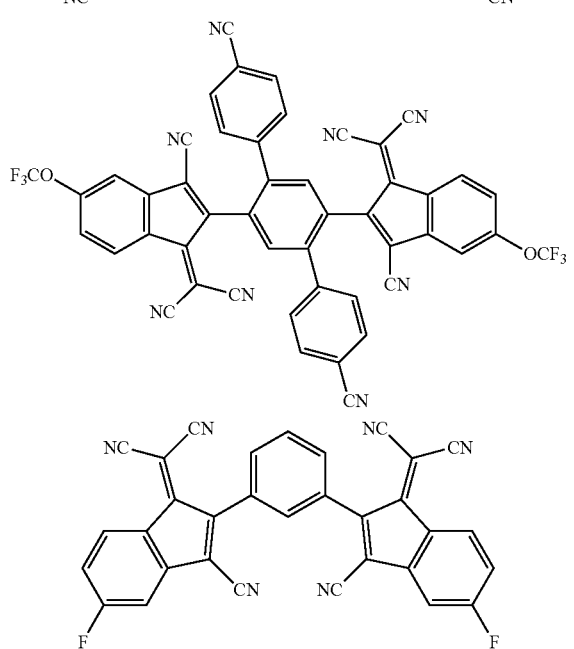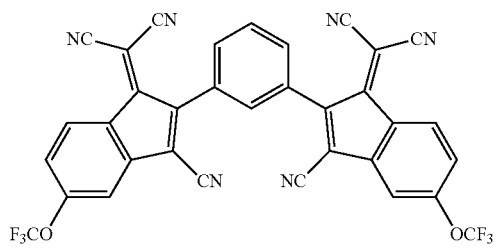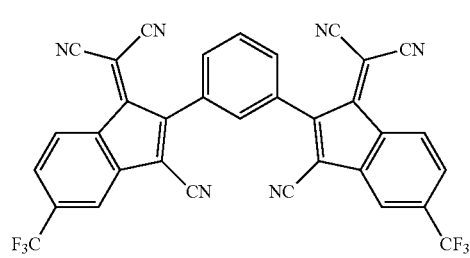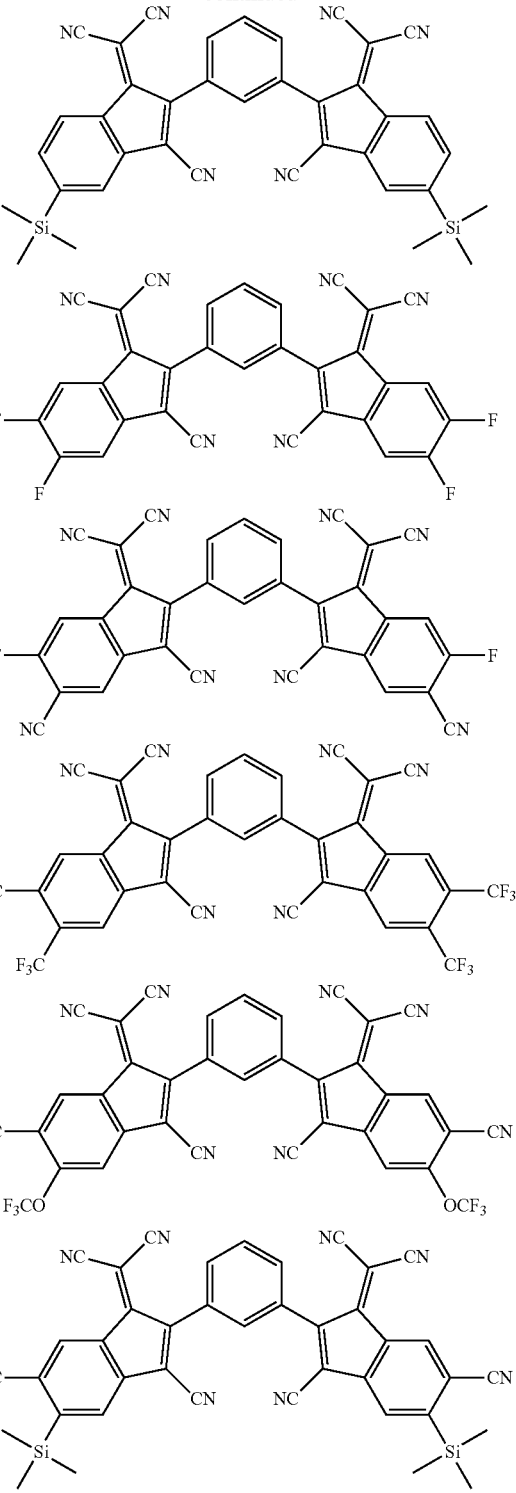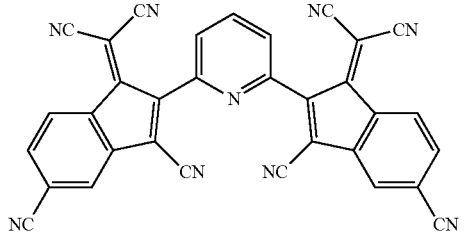

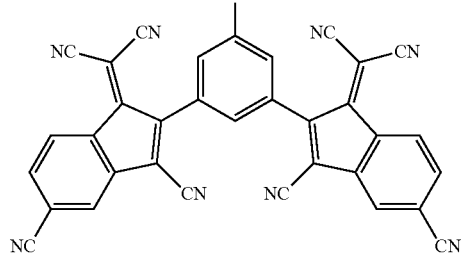
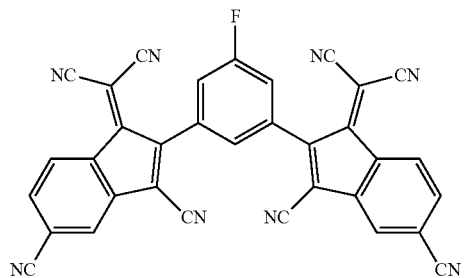
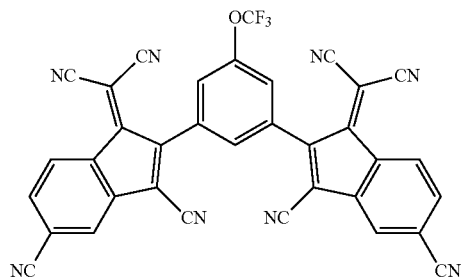
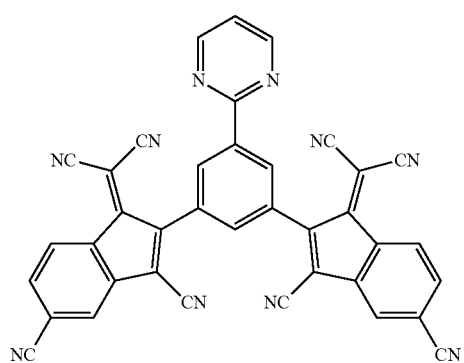
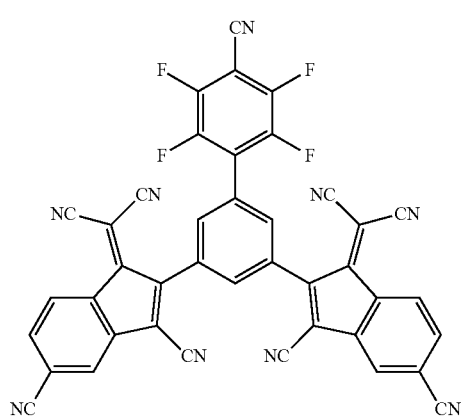
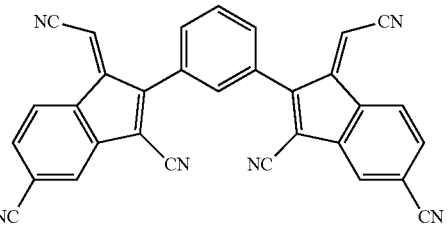
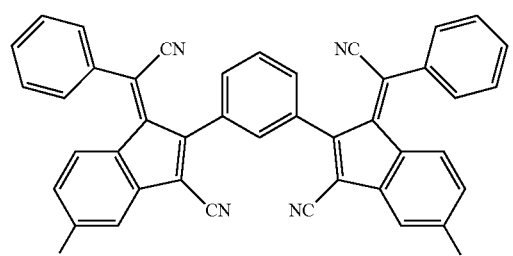
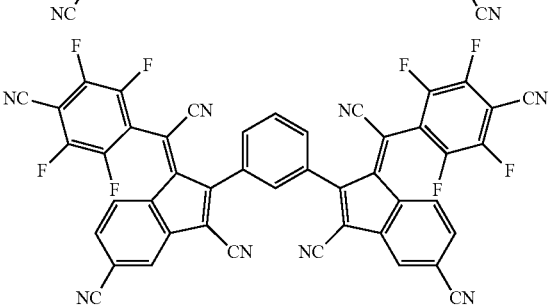
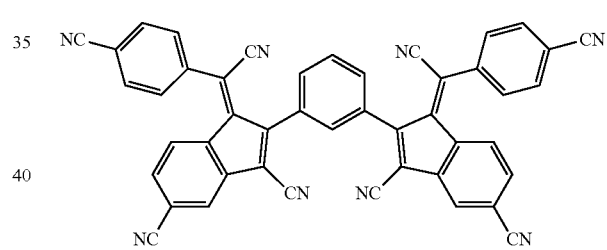
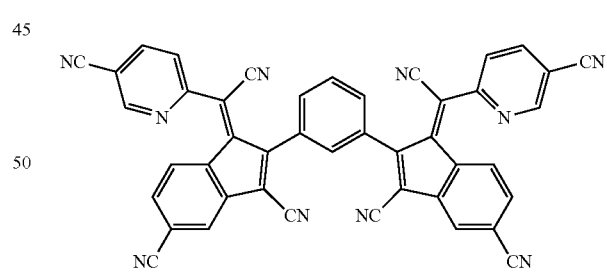
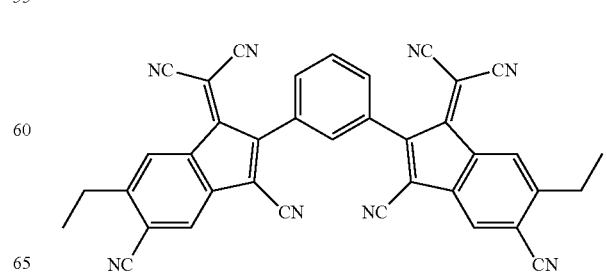

-continued

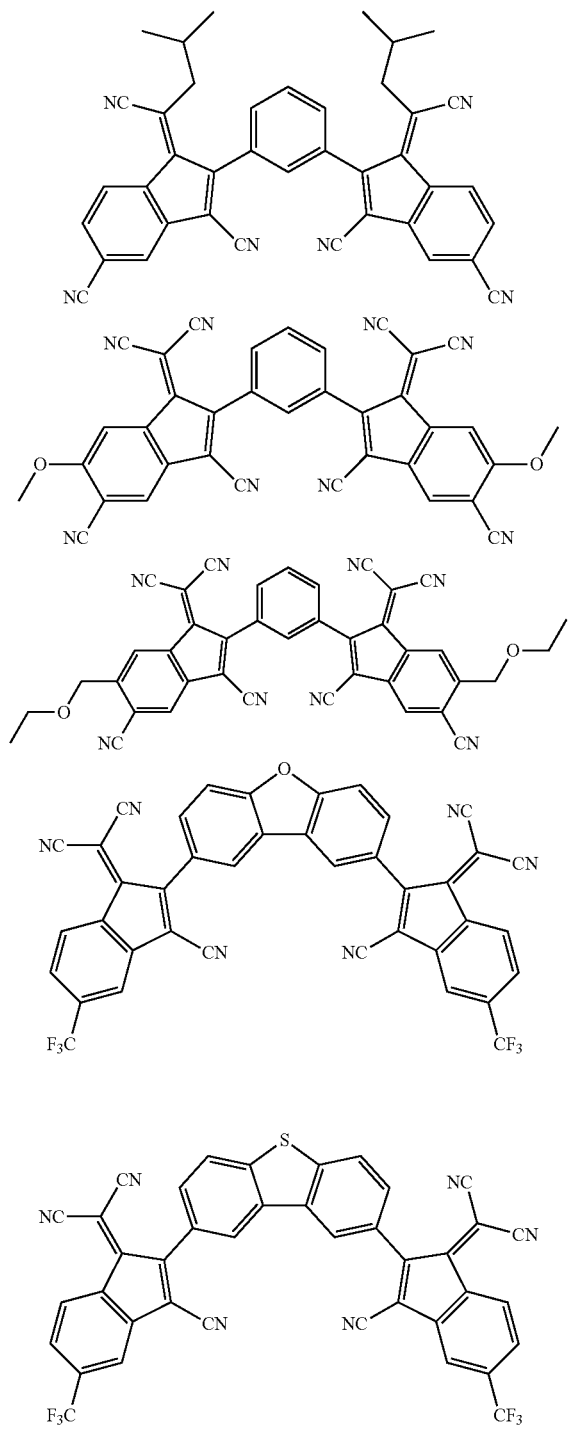

-continued

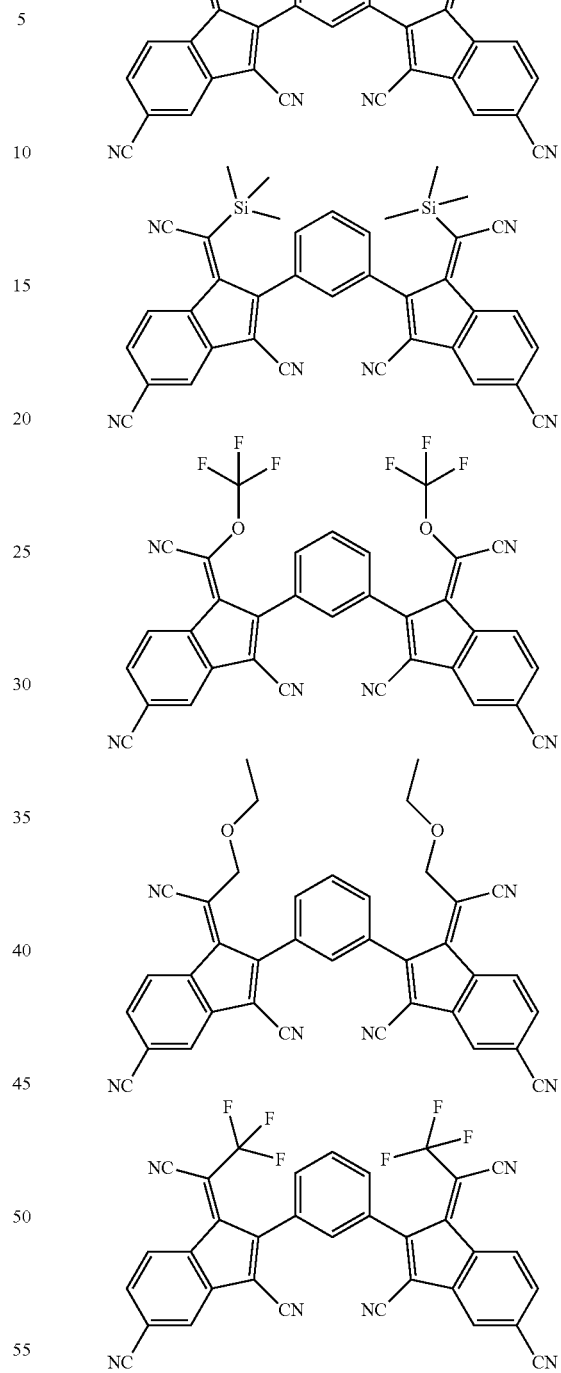

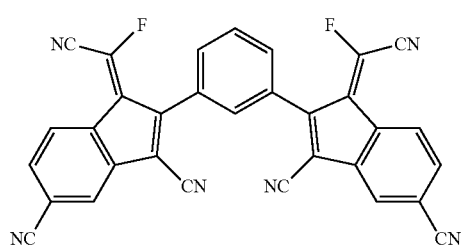

As mentioned above, the organic compound of the present invention has the strong (high) electron withdrawing property and high thermal stability. In addition, the organic compound of the present invention has the low LUMO level.

Namely, the LUMO level of the organic compound is substantially equal to or less than the HOMO level of the HTL 220 or the host material in the HIL 210. Accordingly, the electron transporting efficiency in the organic light emitting diode D, which includes the organic compound of the Formula 1 in the HIL 210, is improved such that the driving voltage is decreased and the emitting efficiency is increased.

Synthesis

1. Synthesis of Compound A-1

(1) compound A-1-a

[Reaction Formula 1-1]

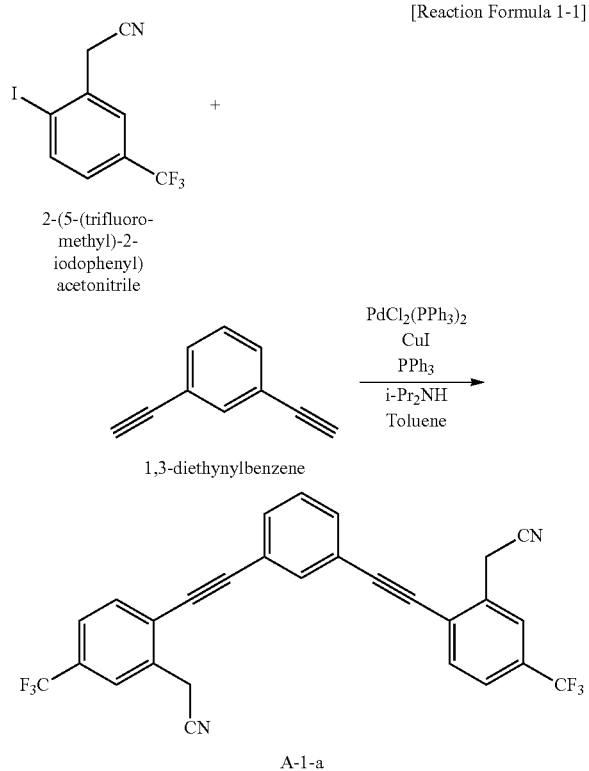

1,3-diethynylbenzene (0.1 mol), PdCl2(PPh3)2 (4 mmol), CuI (4 mmol), PPh3 (8 mmol) and i-Pr2NH (0.2 mol) were input into the 2-neck flask (250 ml) and stirred under the room temperature. 2-(5-(trifluoromethyl)-2-iodophenyl)acetonitrile (0.22 mol) was input into the mixture and stirred under the room temperature for 24 hours. The mixture was extracted with water/EA (ethylene acetate) to obtain an organic layer, and the organic layer was dried using MgSO4. A column-chromatography was performed onto the resultant such that the compound A-1-a of the solid state was obtained. (25.6 g, 52%)

(2) compound A-1-b

[Reaction Formula 1-2]

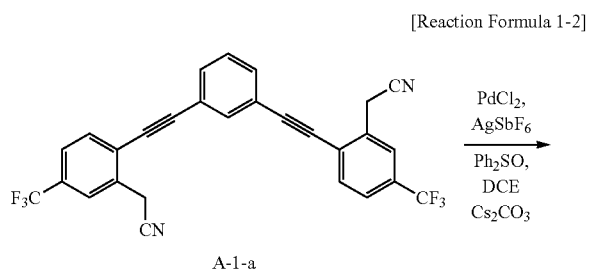

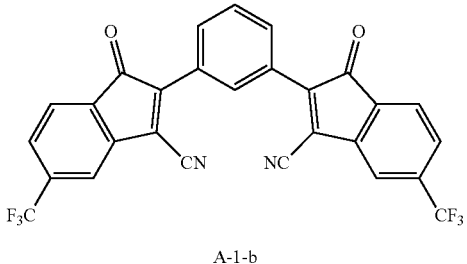

The compound A-1-a (0.052 mol), PdCl2 (10.4 mmol), AgSbF6 (15.6 mmol) and Ph2SO (0.3 mol) were dissolved with dichloroethane (DCE) in the 2-neck flask (250 ml) and stirred under the temperature of 60° C. for 24 hours. Cs2CO3 (0.15 mol) was additionally added into the mixture, and the mixture was stirred for 12 hours. After completion of the reaction, the mixture was extracted using CH2Cl2, and CH2Cl2 was completely removed. The mixture was input into 35% HCl solution and stirred for 2 hours. The mixture was extracted using CH2Cl2/NH4Cl (aqueous) to obtain an organic layer, and the organic layer was dried using MgSO4. A column-chromatography was performed onto the resultant such that the compound A-1-b of the solid state was obtained. (9.2 g, 34%)

(3) compound A-1

[Reaction Formula 1-3]

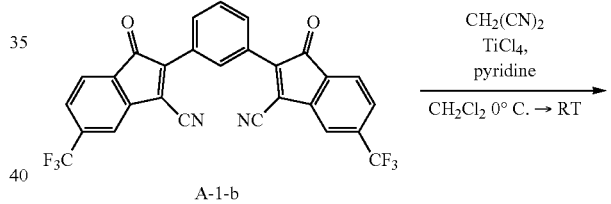

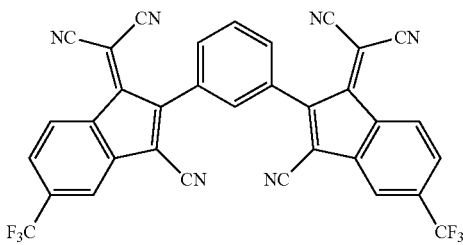

The compound A-1-b (17.7 mmol), malononitrile (0.106 mol) and CH2Cl2 were input into the 2-neck flask (100 ml) and stirred under the argon condition for 30 minutes. TiCl4 (0.106 mol) was slowly dropped, and pyridine (0.13 mol) was added. The mixture was stirred under the room temperature. After completion of the reaction, the mixture was extracted using $CH_2Cl_2$/$NH_4Cl$ (aqueous) to obtain an organic layer, and the organic layer was dried using $MgSO_4$. A column-chromatography was performed onto the resultant such that the compound A-1 of the solid state was obtained. (4.68 g, 43%)

2. Compound A-2

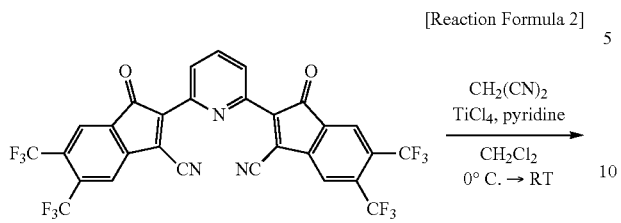

The compound A-2-b was used instead of the compound A-1-b such that the compound A-2 (28%) was obtained.

3. Compound A-3

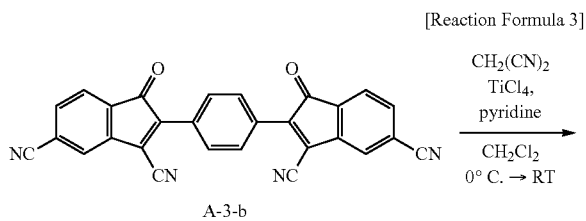

The compound A-3-b was used instead of the compound A-1-b such that the compound A-3 (49%) was obtained.

4. Compound A-4

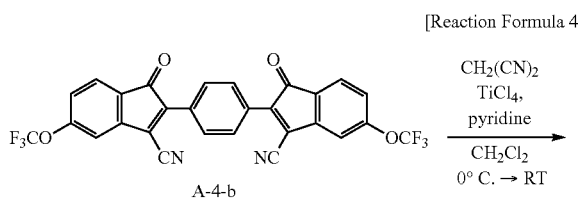

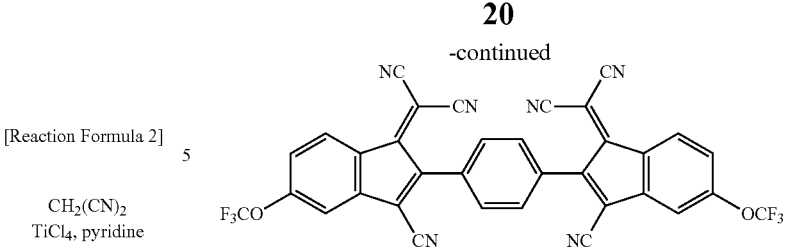

The compound A-4-b was used instead of the compound A-1-b such that the compound A-4 (43%) was obtained.

The energy levels of the compound A-1, A-2, A-3 and A-4, NPD, which may be used for the HTL or the host material of the HIL, and HAT-CN, which may be used for the dopant of the HIL, are measured and listed in Table 1.

TABLE 1

|  | HOMO [eV] | LUMO [eV] | Bandgap [eV] |
|---|---|---|---|
| A-1 | −7.73 | −5.58 | 2.15 |
| A-2 | −8.03 | −5.79 | 2.24 |
| A-3 | −7.79 | −5.75 | 2.04 |
| A-4 | −7.45 | −5.44 | 2.01 |
| HAT-CN | −8.68 | −5.2 | 3.48 |
| NPD | −5.4 | −2.3 | 3.1 |

As shown in Table 1, the LUMO level of the compound A-1, A-2, A-3 and A-4 is lower than the HOMO level of the compound NPD such that the HIL including the organic compound of the present invention has improved hole injection property. On the other hand, the LUMO level of the compound HAT-CN is higher than the HOMO level of the compound NPD such that the hole injection property of the HIL including the compound HAT-CN is degraded.

Organic Light Emitting Diode

1. Example 1 (Ex1)

An ITO layer is deposited and patterned on a substrate and washed to form the anode (2 mm*2 mm). The substrate is loaded in a vacuum chamber having a base pressure of 5~7*10-8, and layers are sequentially deposited as below.

(1) the HIL (the compound A-1, 50 Å), (2) the HTL (NPD, 800 Å), (3) the EML (host (Formula 3-1) and dopant (Formula 3-2, 5 wt % doping), 300 Å), (4) the ETL (compound of Formula 3-3, 200 Å), (5) the EIL (LiF, 5 Å) and (11) the cathode (Al, 1000 Å).

2. Example 2 (Ex2)

Instead of the compound A-1 in "Example 1", the compound NPD and the compound A-1 as a dopant (10 wt % doping) are used.

3. Example 3 (Ex3)

Instead of the compound A-1 in "Example 1", the compound A-2 is used.

4. Example 4 (Ex4)

Instead of the compound A-1 in "Example 1", the compound NPD and the compound A-2 as a dopant (10 wt % doping) are used.

5. Example 5 (Ex5)

Instead of the compound A-1 in "Example 1", the compound A-3 is used.

6. Example 6 (Ex6)

Instead of the compound A-1 in "Example 1", the compound NPD and the compound A-3 as a dopant (10 wt % doping) are used.

7. Example 7 (Ex7)

Instead of the compound A-1 in "Example 1", the compound A-4 is used.

8. Example 8 (Ex8)

Instead of the compound A-1 in "Example 1", the compound NPD and the compound A-4 as a dopant (10 wt % doping) are used.

9. Comparative Example 1 (Ref1)

Instead of the compound A-1 in "Example 1", the compound HAT-CN is used.

10. Comparative Example 2 (Ref2)

Instead of the compound A-1 in "Example 1", the compound NPD and the compound HAT-CN as a dopant (10 wt % doping) are used.

11. Comparative Example 3 (Ref3)

The HIL in "Example 1" is omitted.

[Formula 3-1]

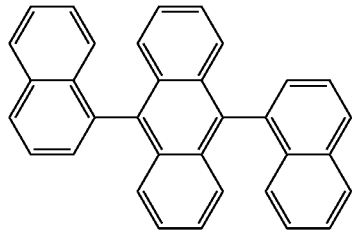

[Formula 3-2]

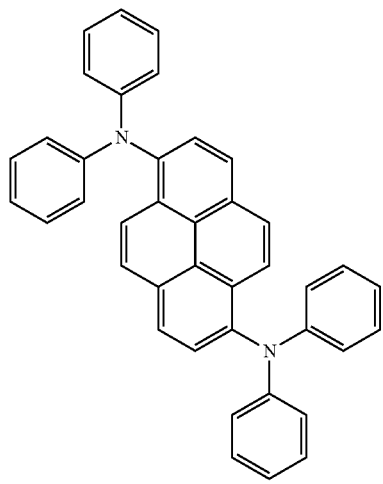

[Formula 3-3]

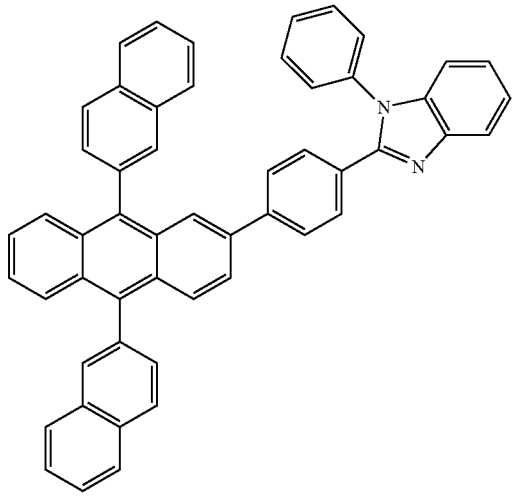

The driving voltage, the emitting efficiency and the external quantum efficiency (EQE) of the organic light emitting diodes of "Ex1" to "Ex8" and "Ref1" to "Ref3" are measured and listed in Table 2.

TABLE 2

|  | Voltage [V] | Efficiency [Cd/A] | EQE [%] |
|---|---|---|---|
| Ex1 | 3.9 | 4.8 | 5.0 |
| Ex2 | 3.9 | 4.9 | 4.9 |
| Ex3 | 3.8 | 4.7 | 5.2 |
| Ex4 | 3.9 | 4.6 | 5.1 |
| Ex5 | 3.7 | 5.0 | 5.5 |
| Ex6 | 3.7 | 4.9 | 5.4 |
| Ex7 | 4.0 | 4.7 | 4.9 |
| Ex8 | 4.1 | 4.6 | 4.7 |
| Ref1 | 4.0 | 4.5 | 4.9 |
| Ref2 | 5.9 | 3.1 | 3.9 |
| Ref3 | 7.0 | 1.5 | 1.9 |

As shown in Table 2, the driving properties, e.g., the driving voltage, the emitting efficiency and the external quantum efficiency, of the organic light emitting diode of the present invention are improved.

Figure 3A:
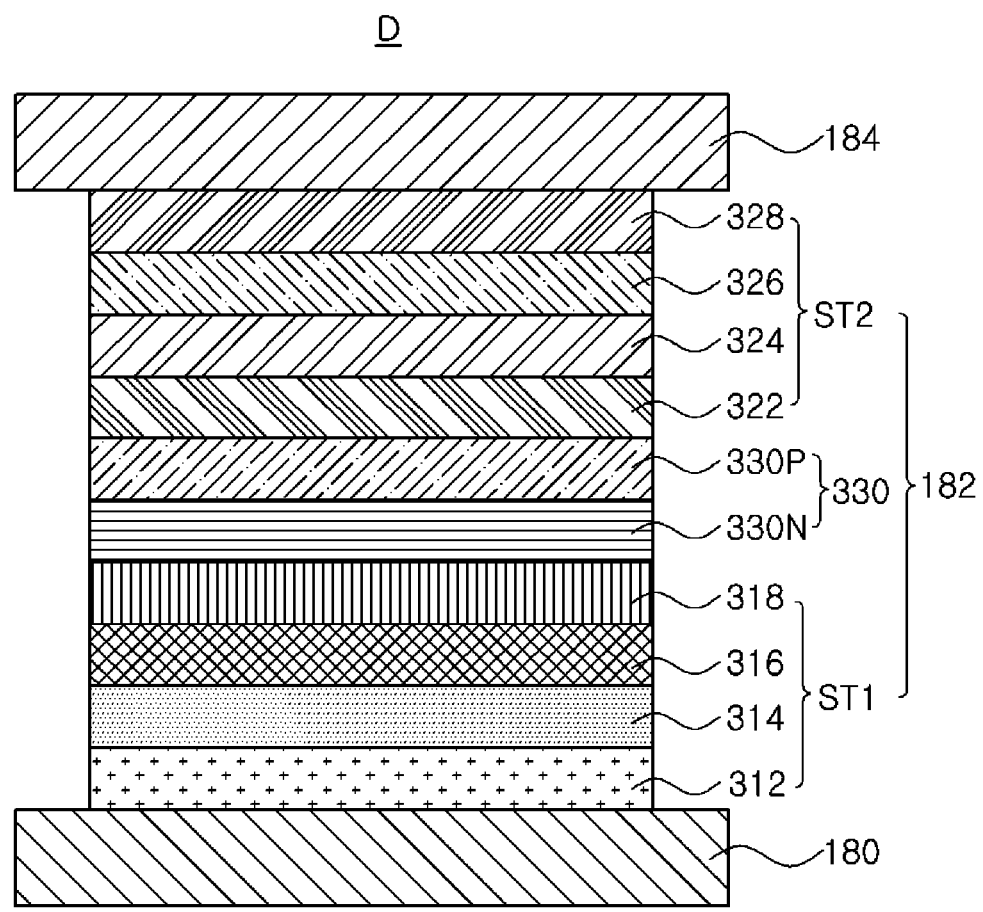
FIGS. 3A and 3B are schematic cross-sectional views of an organic light emitting diode of a tandem structure according to a second embodiment of the present invention, respectively.
Figure 3B:
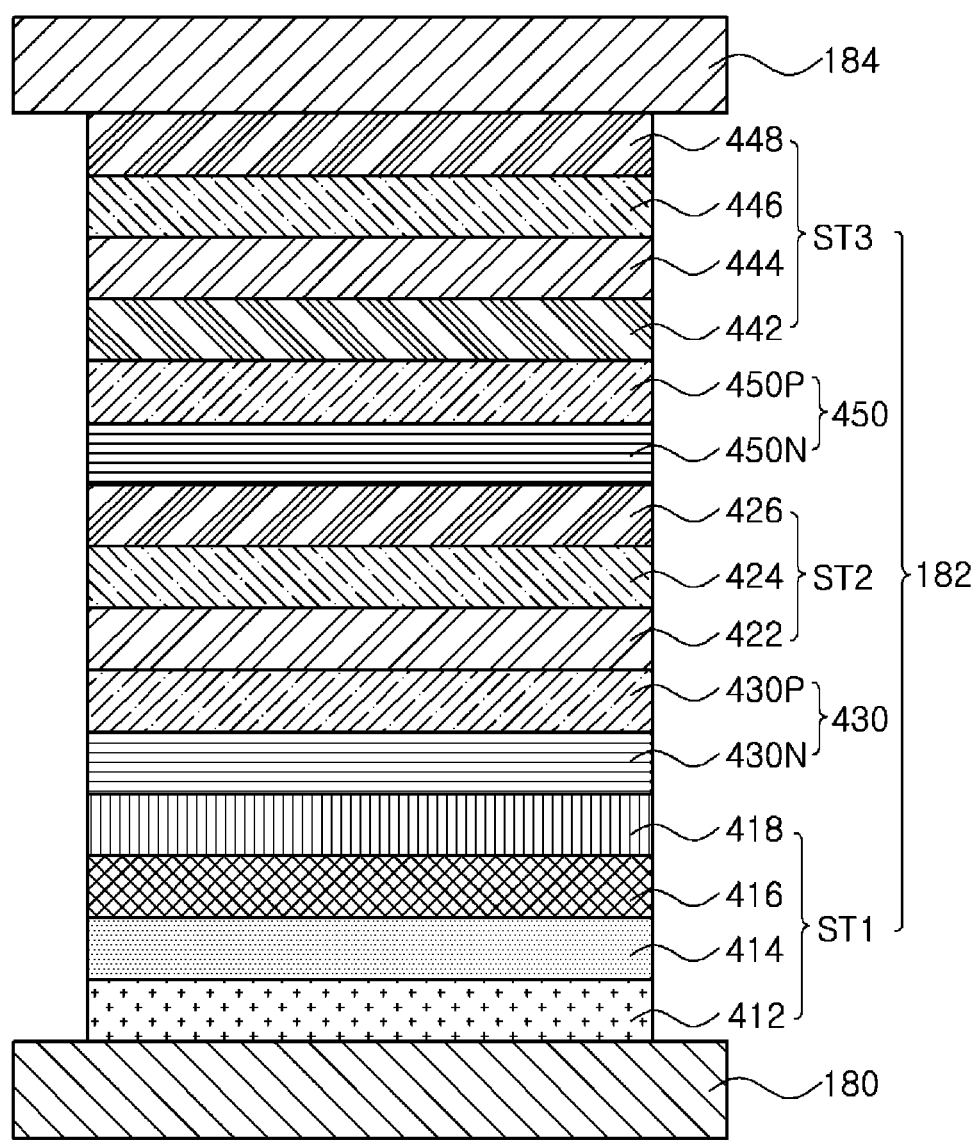

FIGS. 3A and 3B are schematic cross-sectional views of an organic light emitting diode of a tandem structure according to a second embodiment of the present invention, respectively.

As shown in FIG. 3A, the organic light emitting diode D includes a first electrode 180, a second electrode 184, an organic emitting layer 182 between the first and second electrodes 180 and 184 and including first and second emitting parts ST1 and ST2 and a charge generation layer (CGL) 330.

As mentioned above, the first electrode 180 is the anode for injecting a hole and includes a high work function conductive material, e.g., ITO, IZO or ZO. The second electrode 184 is the cathode for injecting an electron and includes a low work function conductive material, e.g., Al, Mg or Al—Mg alloy.

The CGL 330 is positioned between the first and second emitting parts ST1 and ST2. Namely, the first emitting part ST1, the CGL 330 and the second emitting part ST2 are sequentially stacked on the first electrode 180. In other words, the first emitting part ST1 is positioned between the first electrode 180 and the CGL 330, and the second emitting part ST2 is positioned between the second electrode 184 and the CGL 330.

The first emitting part ST1 may include a hole injection layer (HIL) 312, a first hole transporting layer (HTL) 314, a first emitting material layer (EML) 316 and a first electron transporting layer (ETL) 318 sequentially stacked on the first electrode 180. Namely, the HIL 312 and the first HTL 314 are positioned between the first electrode 180 and the first EML 316, and the HIL 312 is positioned between the first electrode 180 and the first HTL 314. In addition, the first ETL 318 is positioned between the first EML 316 and the CGL 330.

A hole injection from the first electrode 180 into the first EML 316 is improved by the HIL 312. The HIL 312 may include the organic compound of the above Formula 1. The HIL 312 may be formed of the organic compound without other compounds or may be formed of the organic compound as a dopant with a host material.

Alternatively, the HIL 312 may include at least one selected from the group consisting of copper phthalocyanine (CuPC), poly(3,4)-ethylenedioxythiophene) (PEDOT) and polyaniline.

The HIL 312 may have a thickness of about 1 to 150 nm. The hole injection property may be improved with a thickness above 1 nm, and an increase of the driving voltage resulting from an increase of a thickness of the HIL 312 may be prevented with a thickness below 150 nm.

A hole transporting is improved by the first HTL 314. The first HTL 314 may include at least one selected from the group consisting of N,N'-bis(naphthalen-1-yl)-N,N'-bis(phenyl)-2,2'-dimethylbenzidine (NPD), N,N'-bis-(3-methylphenyl)-N,N'-bis-(phenyl)-benzidine (TPD), 2,2',7,7'-tetrakis(N,N-diphenylamino)-9,9'-spirofluorene (spiro-TAD) and 4,4',4"-Tris(N-3-methylphenyl-N-phenylamino)-triphenylamine (MTDATA), but it is not limited thereto.

The first HTL 314 may have a thickness of about 1 to 150 nm. The hole transporting property may be improved with a thickness above 1 nm, and an increase of the driving voltage resulting from an increase of a thickness of the first HTL 314 may be prevented with a thickness below 150 nm.

The first EML 316 may be a blue EML. Alternatively, the first EML 316 may be a red EML, a green EML or a yellow EML.

An electron transporting is improved by the first ETL 318. The first ETL 318 may include a compound represented by Formula 3-3, tris(8-hydroxy-quinolinato)aluminum (Alq3), 2-(4-biphenyl)-5-(4-tertbutylphenyl)-1,3,4-oxadiazole (PBD), 3-(4-biphenyl)-4-phenyl-5-tertbutylphenyl-1,2,4-triazole (TAZ) or Bis(2-methyl-8-quinolinolate)-4-(phenylphenolato)aluminum (BAlq), but it is not limited thereto.

The first ETL 318 may have a thickness of about 1 to 150 nm. The electron transporting property may be improved with a thickness above 1 nm, and an increase of the driving voltage resulting from an increase of a thickness of the first ETL 318 may be prevented with a thickness below 150 nm.

The second emitting part ST2 may include a second HTL 322, a second EML 324, a second ETL 326 and an electron injection layer (EIL) 328. The second HTL 322 is positioned between the CGL 330 and the second EML 324, and the second ETL 326 is positioned between the second EML 324 and the second electrode 184. In addition, the EIL 328 is positioned between the second ETL 326 and the second electrode 184.

The second HTL 322 and the second ETL 326 may be same as or different from the first HTL 314 and the first ETL 318 in the first emitting part ST1, respectively. The EIL 328 may be omitted according to the structure or property of the organic light emitting diode.

The second EML 324 may be red, green, blue or yellow-green EML. For example, when the first EML 316 is the blue EML, the second EML 324 may be yellow-green EML.

An electron injection is improved by the EIL 328. The EIL 328 may include at least one selected from the group consisting of tris(8-hydroxy-quinolinato)aluminum (Alq3), 2-(4-biphenyl)-5-(4-tertbutylphenyl)-1,3,4-oxadiazole (PBD), 3-(4-biphenyl)-4-phenyl-5-tertbutylphenyl-1,2,4-triazole TAZ) and Bis(2-methyl-8-quinolinolate)-4-(phenylphenolato)aluminum (BAlq), but it is not limited thereto.

On the other hand, the EIL 328 may further include a metal compound. For example, the metal compound may be at least one selected from the group consisting of LiF, NaF, KF, RbF, CsF, FrF, BeF2, MgF2, CaF2, SrF2, BaF2 and RaF2, but it is not limited thereto.

The EIL 328 may have a thickness of about 1 to 50 nm. The electron injection property may be improved with a thickness above 1 nm, and an increase of the driving voltage resulting from an increase of a thickness of the EIL 328 may be prevented with a thickness below 50 nm.

The CGL 330 is positioned between the first emitting part ST1 and the second emitting part ST2. Namely, the first and second emitting parts ST1 and ST2 are connected by the CGL 330. The CGL 330 may be a P-N junction type CGL including an N-type CGL 330N and a P-type CGL 330P.

The N-type CGL 330N is positioned between the first ETL 318 and the second HTL 322, and the P-type CGL 330P is positioned between the N-type CGL 330N and the second HTL 322.

The CGL 330 generates a charge or separates a charge into a hole and an electron such that the hole and the electron are provided into the first and second emitting parts ST1 and ST2.

The N-type CGL 330N provides the electron into the first ETL 318 of the first emitting part ST1, and the first ETL 318 provide the electron into the first EML 316 of the first emitting part ST1. On the other hand, the P-type CGL 330P provide the hole into the second HTL 322 of the second emitting part ST2, and the second HTL 322 provide the hole into the second EML 324 of the second emitting part ST2. Accordingly, the emitting efficiency of the organic light emitting diode D including a plurality of EMLs or a plurality of emitting parts is improved, and the driving voltage of the organic light emitting diode D is reduced.

Referring to FIG. 3B, an organic light emitting diode D includes a first electrode 180, a second electrode 184, an organic emitting layer 182 between the first and second electrodes 180 and 184 and including first to third emitting parts ST1, ST2 and ST3 and first and second charge generation layers (CGLs) 430 and 450. Alternatively, four or more emitting parts and three or more CGLs may be disposed between the first and second electrodes 180 and 184.

As mentioned above, the first electrode 180 is the anode for injecting a hole and includes a high work function conductive material, e.g., ITO, IZO or ZO. The second electrode 184 is the cathode for injecting an electron and includes a low work function conductive material, e.g., Al, Mg or Al—Mg alloy.

The first and second CGLs 430 and 450 are positioned between the first and second emitting parts ST1 and ST2 and the second and third emitting parts ST2 and ST3, respectively. Namely, the first emitting part ST1, the first CGL 430, the second emitting part ST2, the second CGL 450 and the third emitting part ST3 are sequentially stacked on the first electrode 180. In other words, the first emitting part ST1 is positioned between the first electrode 180 and the first CGL 430, and the second emitting part ST2 is positioned between the first and second CGLs 430 and 450. In addition, the third emitting part ST3 is positioned between the second electrode 184 and the second CGL 450.

The first emitting part ST1 may include an HIL 412, a first HTL 414, a first EML 416 and a first ETL 418 sequentially stacked on the first electrode 180. Namely, the HIL 412 and the first HTL 414 are positioned between the first electrode 180 and the first EML 416, and the HIL 412 is positioned between the first electrode 180 and the first HTL 414. In addition, the first ETL 418 is positioned between the first EML 416 and the first CGL 430.

The HIL 412 may include the organic compound of the above Formula 1. The HIL 412 may be formed of the organic compound without other compounds or may be formed of the organic compound as a dopant with a host material such as NPD. The organic compound may have a weight % of about 1 to 50 with respect to the host material.

The second emitting part ST2 may include a second HTL 422, a second EML 424 and a second ETL 426. The second HTL 422 is positioned between the first CGL 430 and the second EML 424, and the second ETL 426 is positioned between the second EML 424 and the second CGL 450.

The third emitting part ST3 may include a third HTL 442, a third EML 444, a third ETL 446 and an EIL 448. The third HTL 442 is positioned between the second CGL 450 and the third EML 444, and the third ETL 446 is positioned between the third EML 444 and the second electrode 184. In addition, the EIL 448 is positioned between the third ETL 446 and the second electrode 184.

The first CGL 430 is positioned between the first emitting part ST1 and the second emitting part ST2, and the second CGL 450 is positioned between the second emitting part ST2 and the third emitting part ST3. Each of the first and second CGLs 430 and 450 may be a P-N junction type CGL. The first CGL 430 includes an N-type CGL 430N and a P-type CGL 430P, and the second CGL 450 an N-type CGL 450N and a P-type CGL 450P.

In the first CGL 430, the N-type CGL 430N is positioned between the first ETL 418 and the second HTL 422, and the P-type CGL 430P is positioned between the N-type CGL 430N and the second HTL 422.

In the second CGL 450, the N-type CGL 450N is positioned between the second ETL 426 and the third HTL 442, and the P-type CGL 450P is positioned between the N-type CGL 450N and the third HTL 442.

Each of the first and second CGLs 430 and 450 generates a charge or separates a charge into a hole and an electron such that the hole and the electron are provided into the first to third emitting parts ST1 to ST3.

Namely, in the first CGL 430, the N-type CGL 430N provides the electron into the first ETL 418 of the first emitting part ST1, and the P-type CGL 430P provide the hole into the second HTL 422 of the second emitting part ST2. In addition, in the second CGL 450, the N-type CGL 450N provides the electron into the second ETL 426 of the second emitting part ST2, and the P-type CGL 450P provide the hole into the third HTL 442 of the third emitting part ST3.

Each of the N-type CGLs 330N, 430N and 450N includes an organic material with a metal or an N-type dopant. For example, the metal may be one of Li, Na, K, Rb, Cs, Mg, Ca, Sr, Ba, La, Ce, Sm, Eu, Tb, Dy and Yb. The N-type dopant may be an alkali metal, an alkali metal compound, an alkali earth metal or an alkali earth metal compound. The N-type dopant may be one of Li, Cs, K, Rb, Mg, Na, Ca, Sr, Eu and Yb.

The organic material for the N-type CGLs 330N, 430N and 450N may be a C20 to C60 heterocyclic compound. For example, the organic material may be one of tris(8-hydroxyquinolinato)aluminum (Alq3), triazine derivatives, hydroxyquinolinine derivatives, benzazole derivatives and silole derivatives.

At least one of the P-type CGLs 330P, 430P and 450P may include the organic compound of the present invention. Each of the P-type CGLs 330P, 430P and 450P may be formed of the organic compound without other compounds or may be formed of the organic compound as a dopant with a host material such as NPD. The organic compound may have a weight % of about 1 to 50 with respect to the host material.

The organic compound of the present invention has the strong (high) electron withdrawing property and high thermal stability. In addition, the organic compound of the present invention has the low LUMO level. Namely, the LUMO level of the organic compound is substantially equal to or less than the HOMO level of the second HTLs 322 and 422 and/or the third HTL 442 or the host material in the P-type CGLs 330P, 430P and 450P. Accordingly, when the tandem structure organic light emitting diode D includes the P-type CGLs 330P, 430P and 450P, the hole transporting property is improved such that the driving voltage of the organic light emitting diode D and the OLED device 100 (of FIG. 1) is decreased and the emitting efficiency of the organic light emitting diode D and the OLED device 100 is increased.

Organic Light Emitting Diode

1. Example 9 (Ex9)

An ITO layer is deposited and patterned on a substrate and washed to form the anode (2 mm*2 mm). The substrate is loaded in a vacuum chamber having a base pressure of 5~7*10-8, and layers are sequentially deposited as below.

(1) the HIL (the compound A-1, 50 Å), (2) the first HTL (NPD, 600 Å), (3) the first EML (host (Formula 3-1) and dopant (Formula 3-2, 5 wt % doping), 300 Å), (4) the first ETL (compound of Formula 3-3, 200 Å), (5) the N-type CGL (host (Formula 4) and dopant (Li, 2 wt % doping), 150 Å), (6) the P-type CGL (the compound A-1, 50 Å), (7) the second HTL (NPD, 400 Å), (8) the second EML (host (Formula 3-1) and dopant (Formula 3-2, 5 wt % doping), 300 Å), (9) the second ETL (compound of Formula 3-3, 350 Å), (10) the EIL (LiF, 5 Å) and (11) the cathode (Al, 1000 Å).

2. Example 10 (Ex10)

Instead of the compound A-1 in "Example 9", the compound NPD and the compound A-1 as a dopant (10 wt % doping) are used.

3. Example 11 (Ex11)

Instead of the compound A-1 in "Example 9", the compound A-2 is used.

4. Example 12 (Ex12)

Instead of the compound A-1 in "Example 9", the compound NPD and the compound A-2 as a dopant (10 wt % doping) are used.

5. Example 13 (Ex13)

Instead of the compound A-1 in "Example 9", the compound A-3 is used.

6. Example 14 (Ex14)

Instead of the compound A-1 in "Example 9", the compound NPD and the compound A-3 as a dopant (10 wt % doping) are used.

7. Example 15 (Ex15)

Instead of the compound A-1 in "Example 9", the compound A-4 is used.

8. Example 16 (Ex16)

Instead of the compound A-1 in "Example 9", the compound NPD and the compound A-4 as a dopant (10 wt % doping) are used.

9. Comparative Example 4 (Ref4)

Instead of the compound A-1 in "Example 9", the compound HAT-CN is used.

10. Comparative Example 5 (Ref5)

Instead of the compound A-1 in "Example 9", the compound NPD and the compound HAT-CN as a dopant (10 wt % doping) are used.

11. Comparative Example 6 (Ref6)

The HIL and the P-type CGL in "Example 9" are omitted.

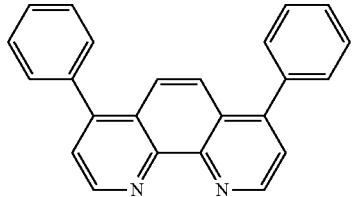

[Formula 4]

The driving voltage, the emitting efficiency and the external quantum efficiency (EQE) of the organic light emitting diodes of "Ex9" to "Ex16" and "Ref4" to "Ref6" are measured and listed in Table 3.

TABLE 3

|  | Voltage [V] | Efficiency [Cd/A] | EQE [%] |
|---|---|---|---|
| Ex9 | 8.5 | 6.9 | 7.8 |
| Ex10 | 8.6 | 7.0 | 8.0 |
| Ex11 | 8.4 | 7.0 | 7.9 |
| Ex12 | 8.4 | 7.1 | 8.0 |
| Ex13 | 8.0 | 7.4 | 8.5 |
| Ex14 | 8.2 | 7.5 | 8.5 |
| Ex15 | 8.6 | 6.8 | 7.7 |
| Ex16 | 8.7 | 6.9 | 7.8 |
| Ref4 | 8.8 | 5.6 | 6.7 |
| Ref5 | 12.9 | 4.7 | 5.3 |
| Ref6 | — | — | — |

As shown in Table 3, the driving properties, e.g., the driving voltage, the emitting efficiency and the external quantum efficiency, of the organic light emitting diode of the present invention are improved.

As mentioned above, the organic compound of the present invention has the strong (high) electron withdrawing property and high thermal stability. In addition, the organic compound of the present invention has the low LUMO level. Accordingly, the organic compound of the present invention in the HIL and/or the P-type CGL easily receives the electron from the HTL or the host material in the HIL such that the electron path is also easily provided or generated. In other words, the electron transporting efficiency in the organic light emitting diode, which includes the organic compound in the HIL and/or the P-type CGL, is improved such that the driving voltage is decreased and the emitting efficiency is increased.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic compound, represented by the following Formula:

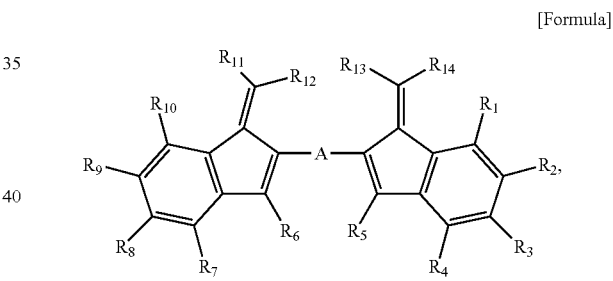

[Formula]

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group, fluorine, tri-fluoro methyl, tri-fluoro methoxy and trimethylsilyl, wherein at least one of $R_1$ to $R_{10}$ is the cyano group, and wherein at least one of $R_{11}$ to $R_{14}$ is the cyano group; and A is selected from substituted or non-substituted $C_6$ to $C_{30}$ aryl and substituted or non-substituted $C_3$ to $C_{30}$ heteroaryl.

2. The organic compound according to claim 1, wherein all of $R_{11}$ to $R_{14}$ are the cyano group.

3. The organic compound according to claim 1, wherein A is one of benzene, naphthalene, pyridine, diazine, dibenzofurane and dibenzothiophene.

4. The organic compound according to claim 1, wherein the organic compound is selected from:

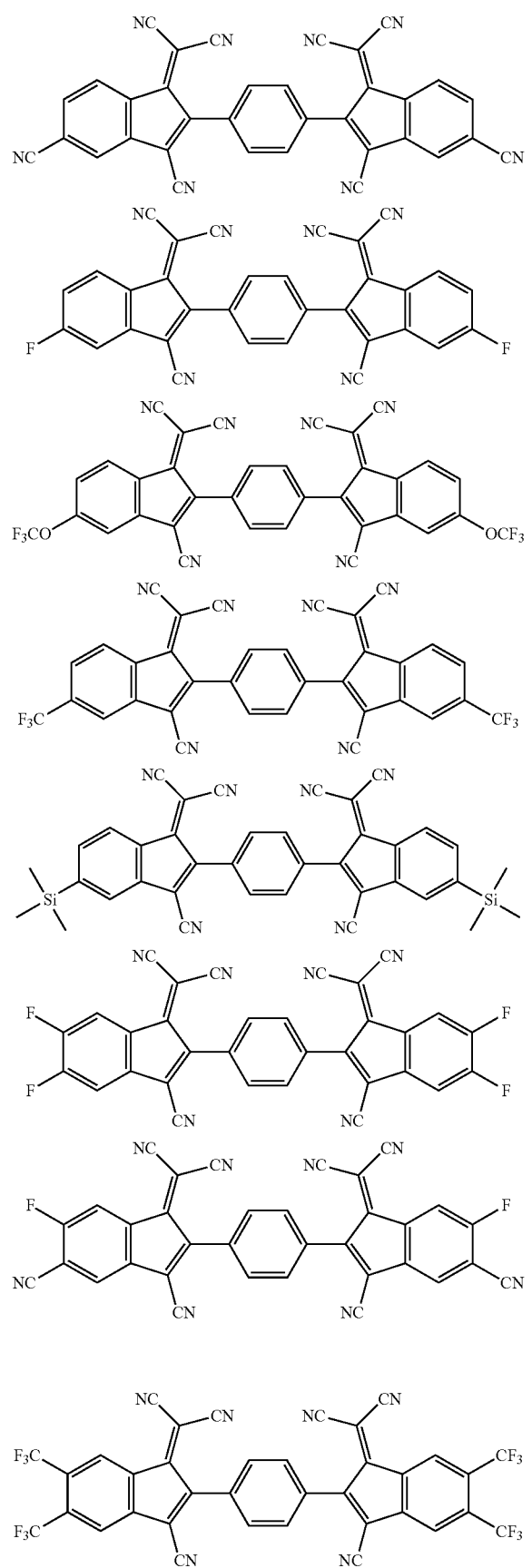
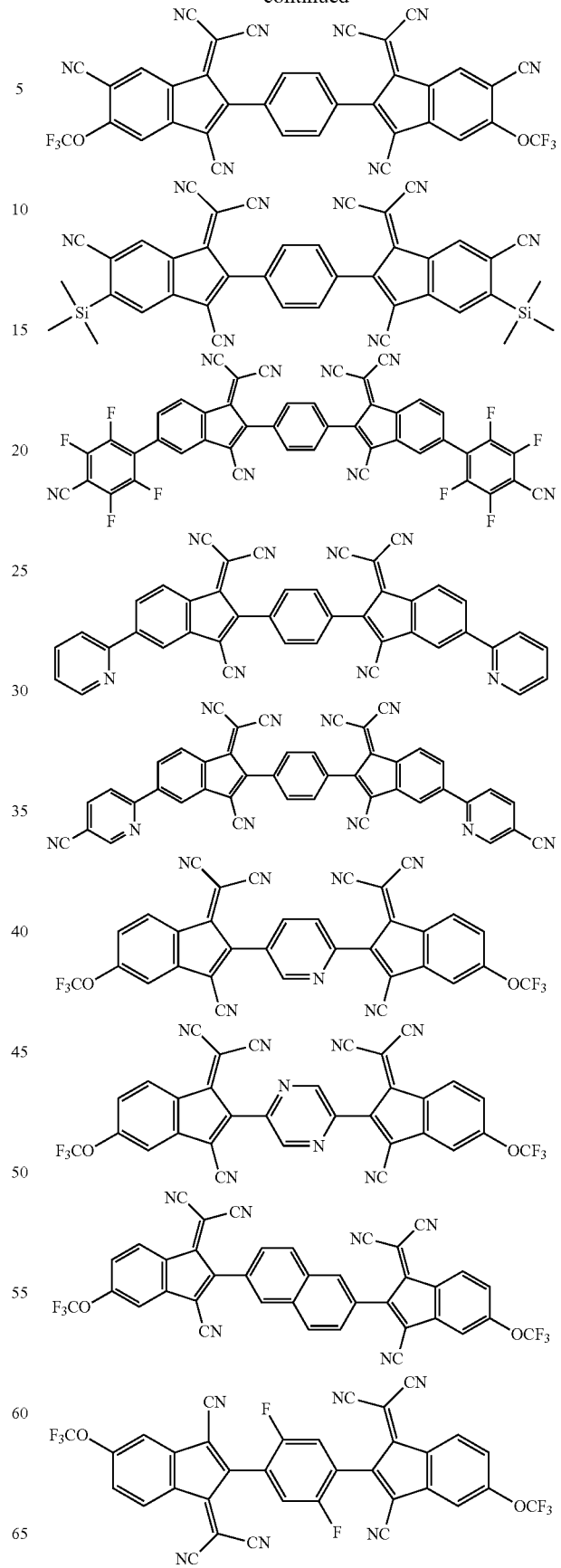

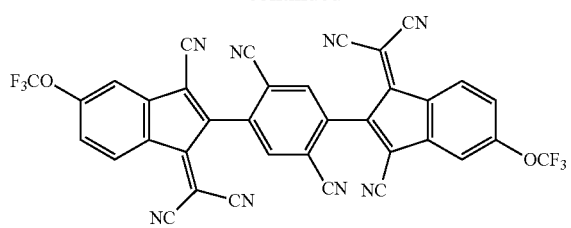
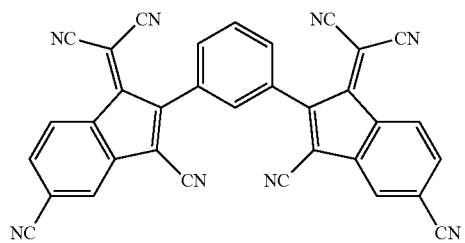
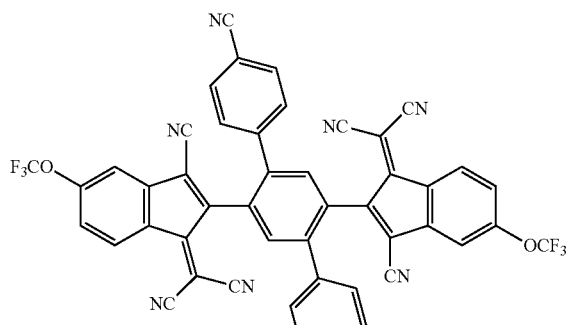
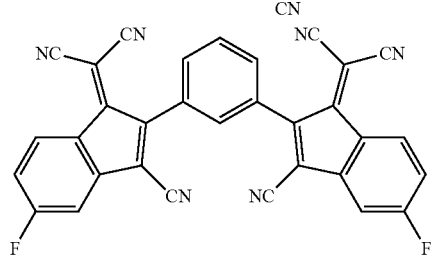
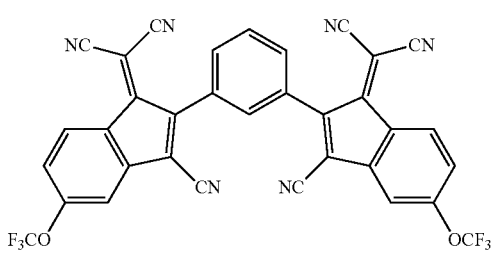
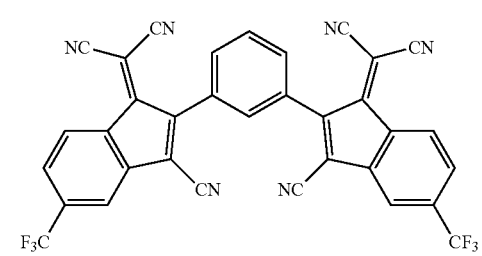
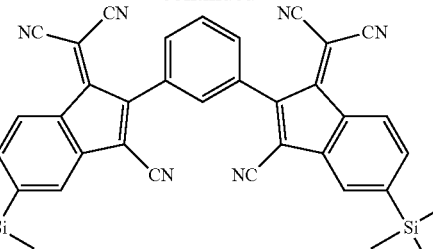
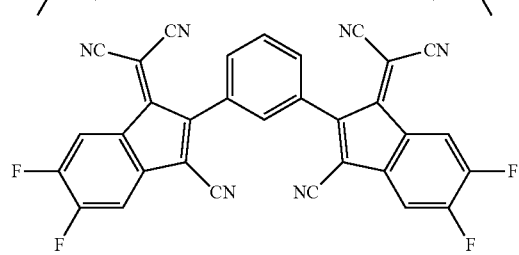
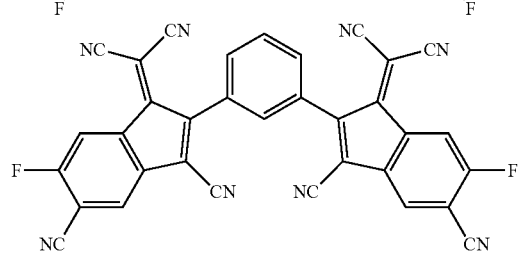
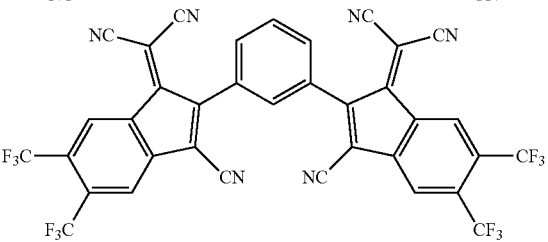
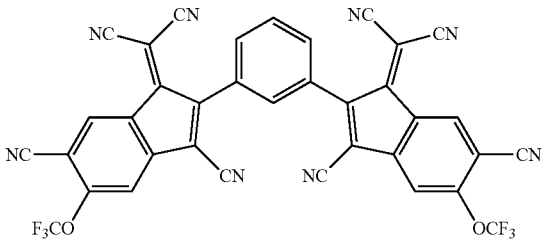
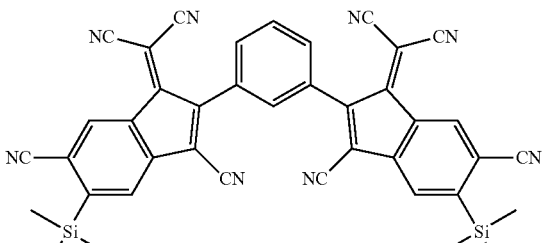
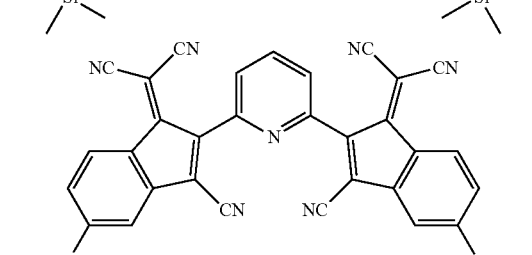

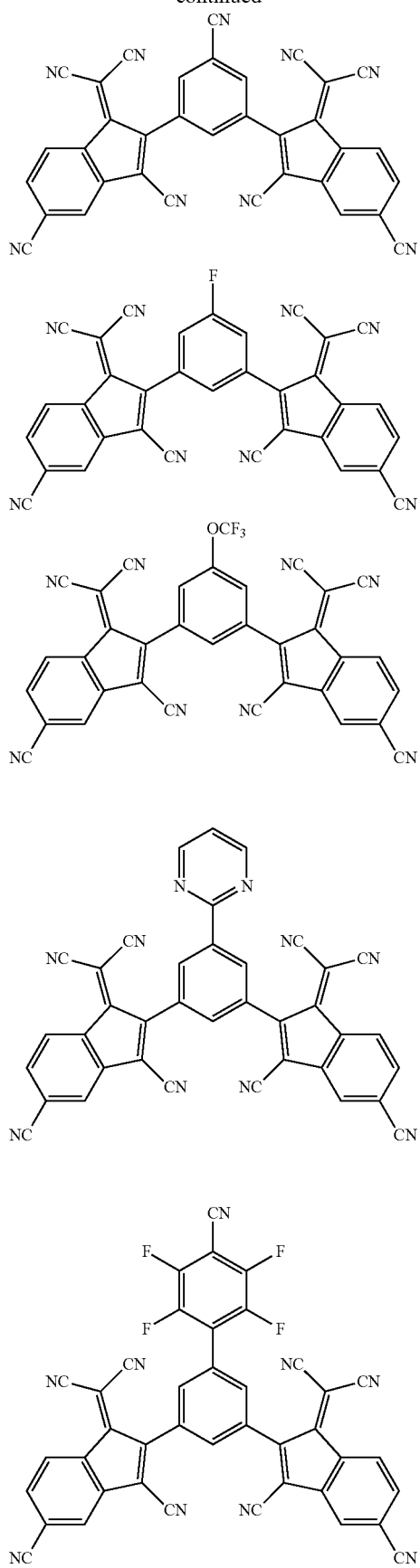
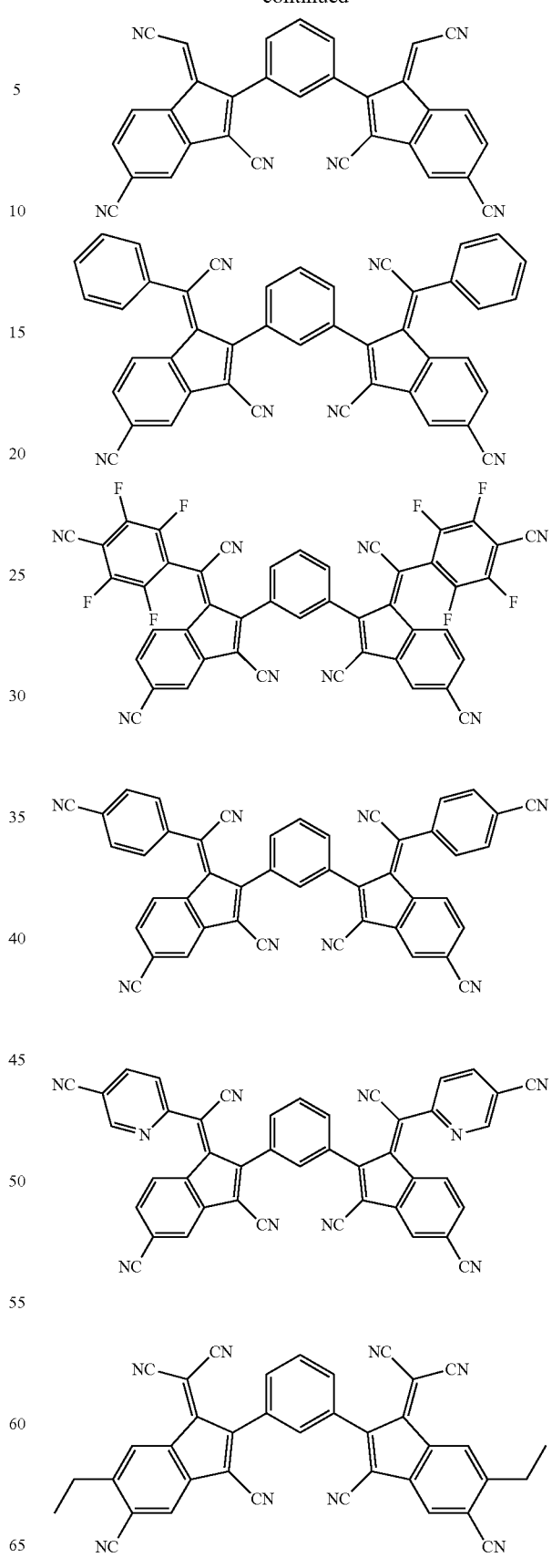

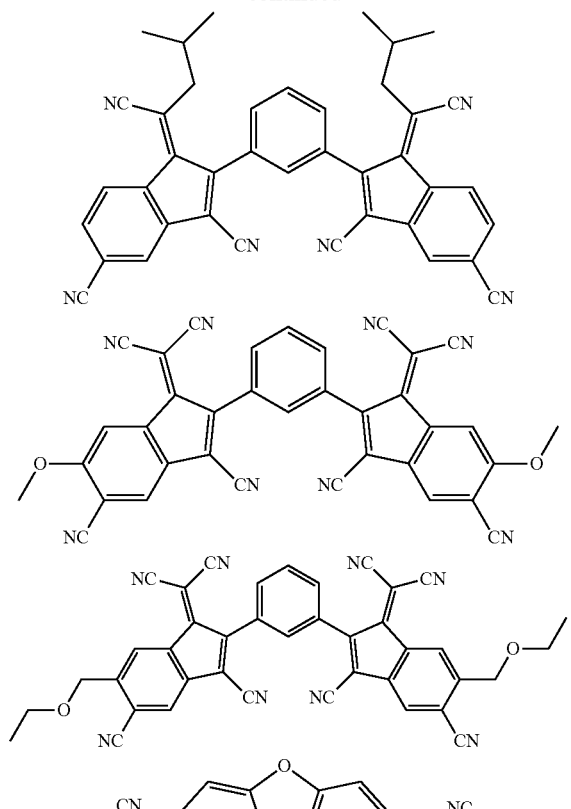

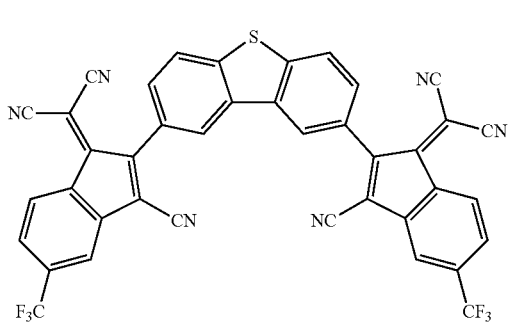

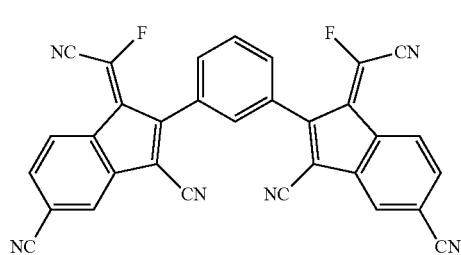

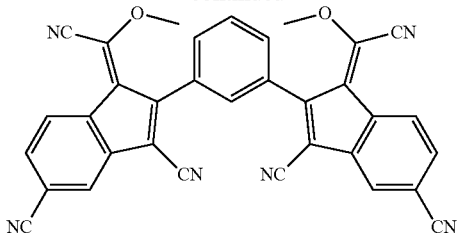

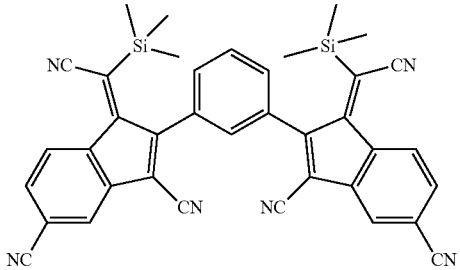

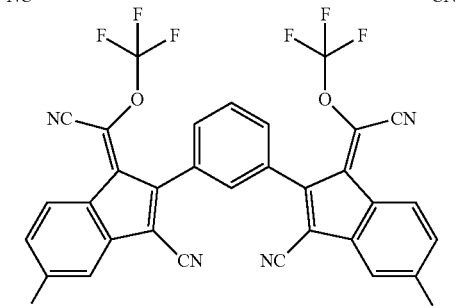

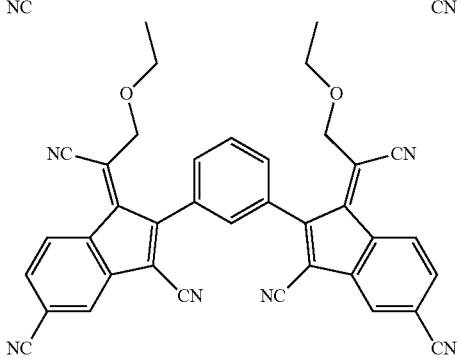

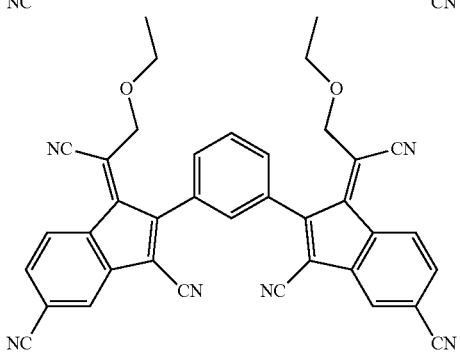

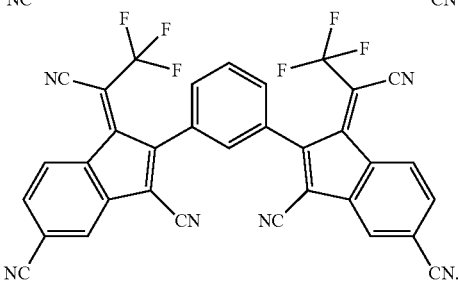

5. An organic light emitting diode, comprising:
first and second electrodes facing each other;
a first emitting part between the first and second electrodes and including a hole injection layer, a first hole transporting layer and a first emitting material layer; and
an electron auxiliary layer between the first emitting part and the second electrode,
wherein the first hole transporting layer includes an organic compound represented by following Formula:

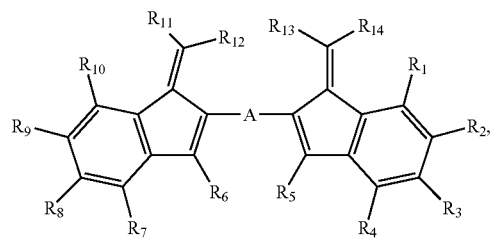

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group, fluorine, tri-fluoro methyl, tri-fluoro methoxy and trimethylsilyl, wherein at least one of $R_1$ to $R_{10}$ is the cyano group, and wherein at least one of $R_{11}$ to $R_{14}$ is the cyano group; and A is selected from substituted or non-substituted $C_6$ to $C_{30}$ aryl and substituted or non-substituted $C_3$ to $C_{30}$ heteroaryl.

6. The organic light emitting diode according to claim 5, wherein all of $R_{11}$ to $R_{14}$ are the cyano group.

7. The organic light emitting diode according to claim 5, wherein A is one of benzene, naphthalene, pyridine, diazine, dibenzofurane and dibenzothiophene.

8. The organic light emitting diode according to claim 5, wherein the organic compound is selected from:

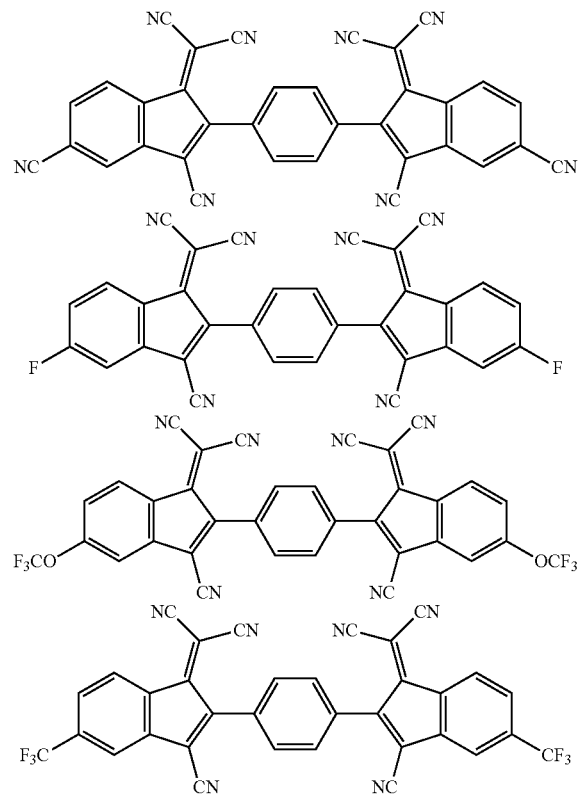

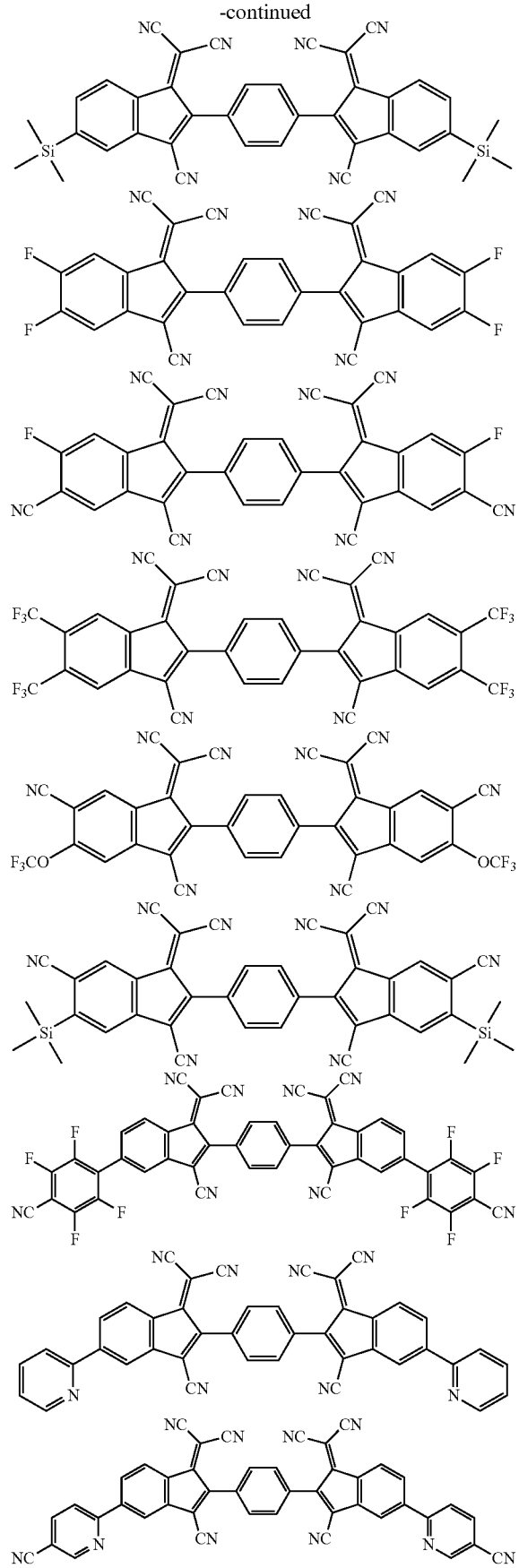

-continued
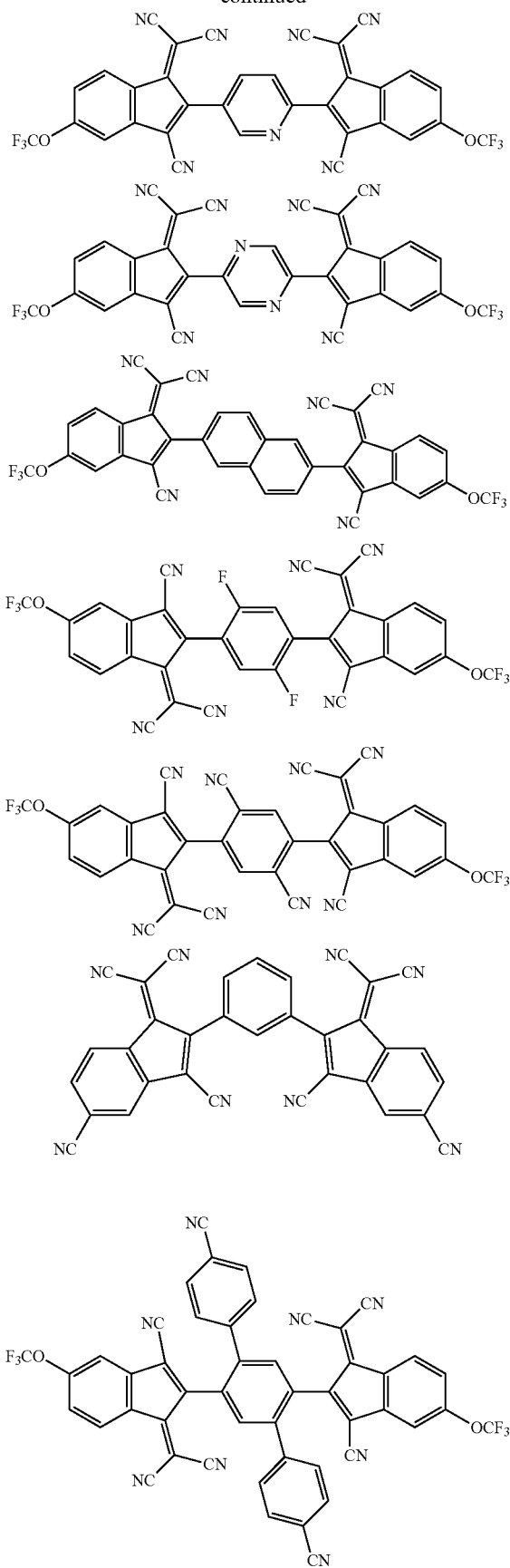
-continued
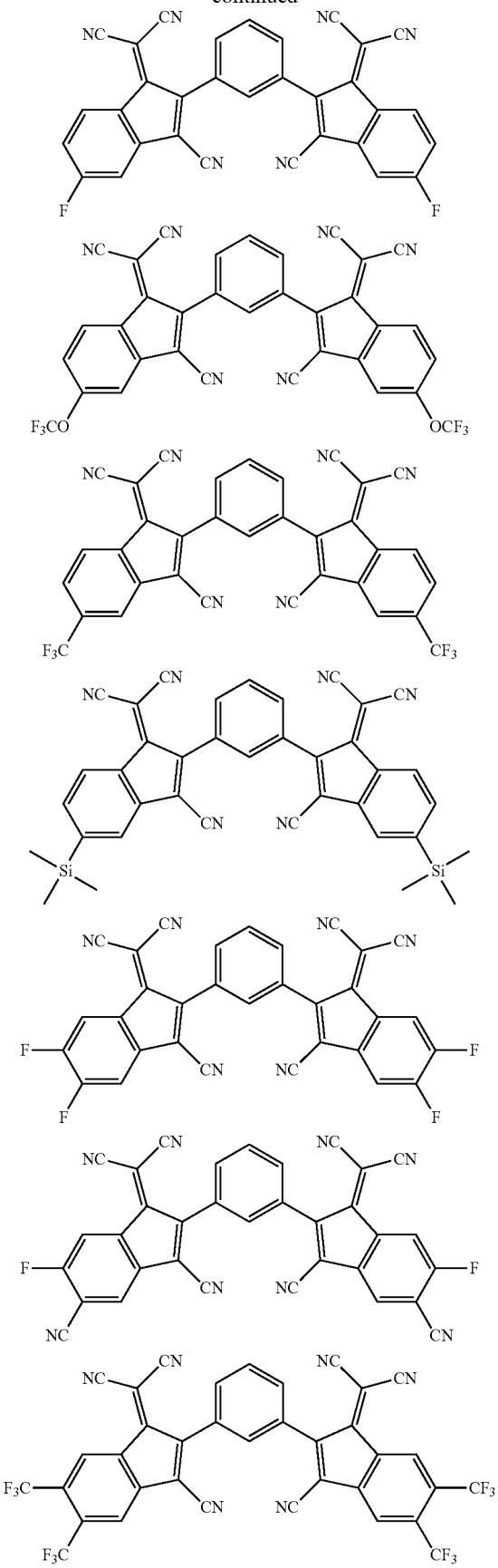

-continued
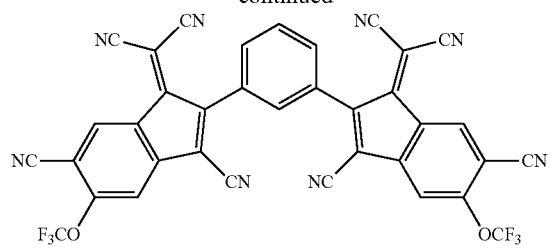
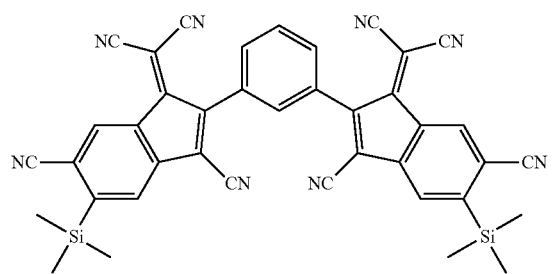
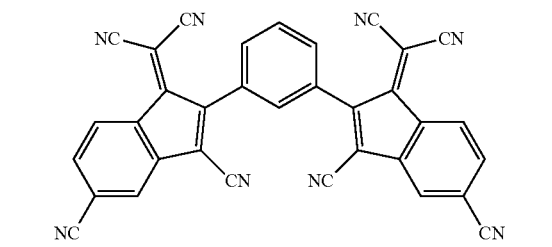
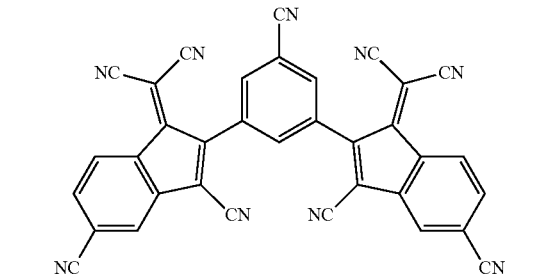
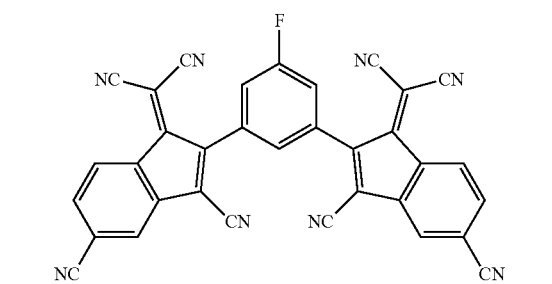
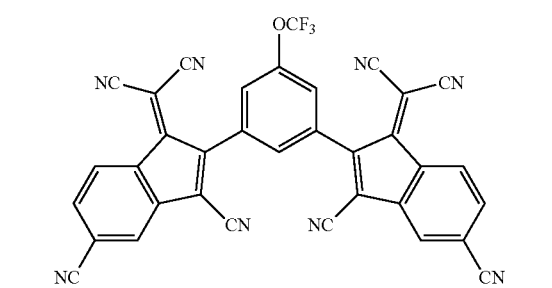
-continued
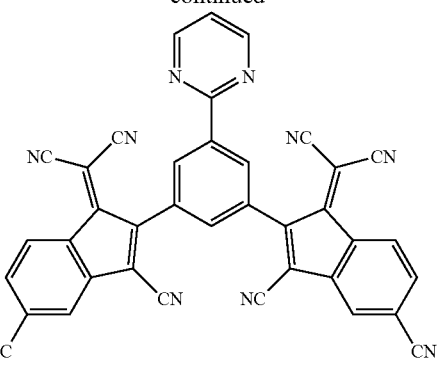
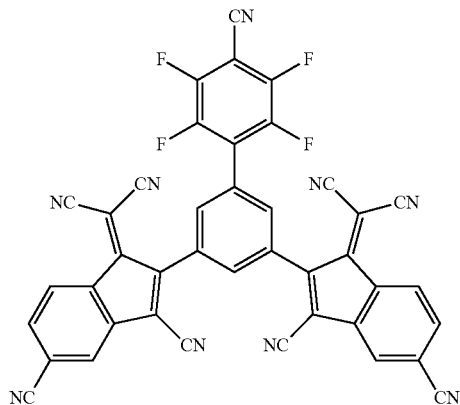
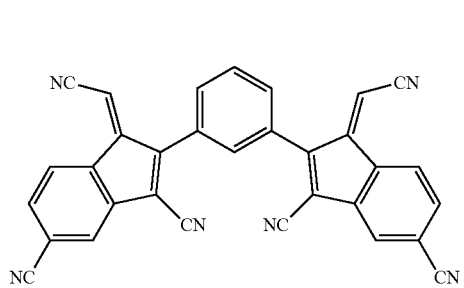
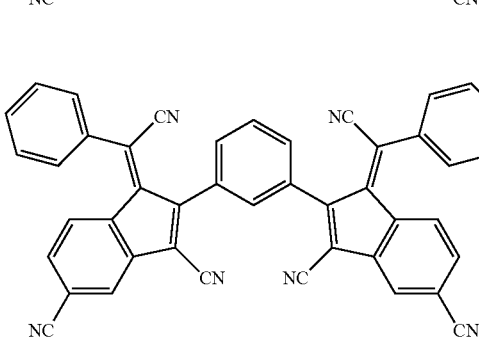
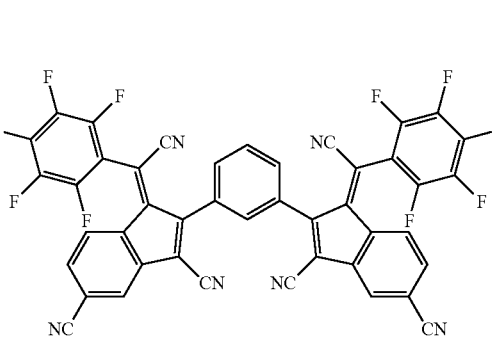

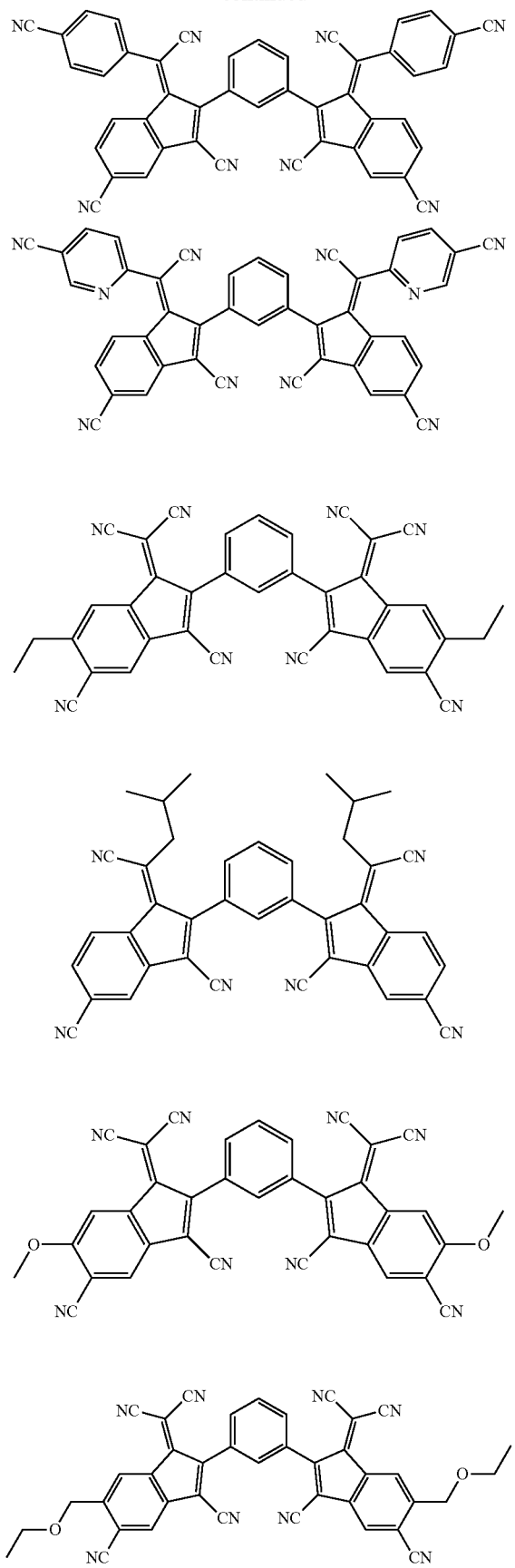
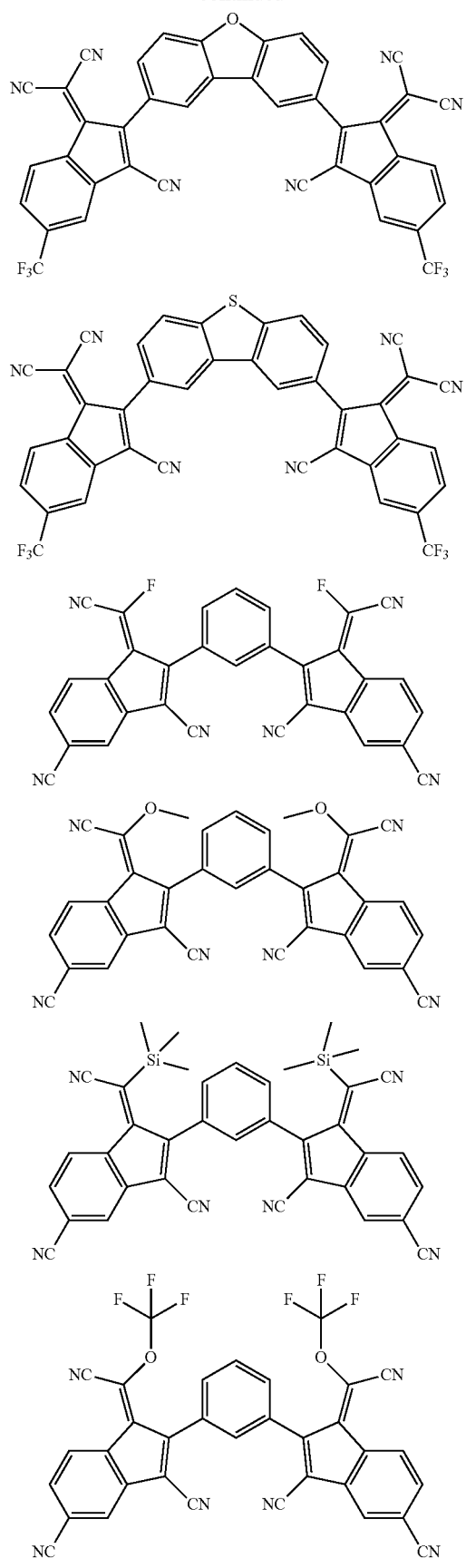

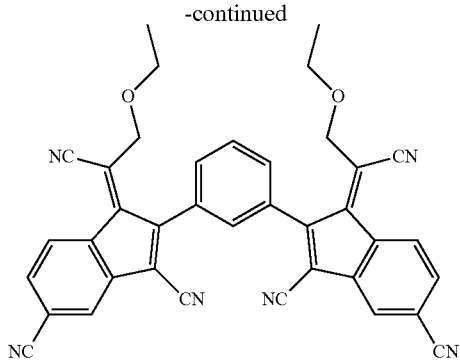

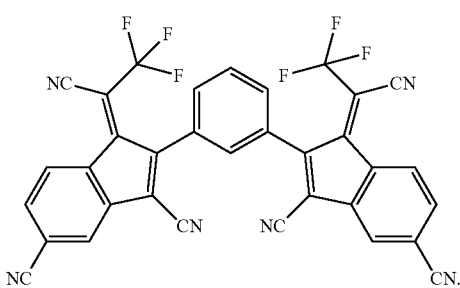

9. The organic light emitting diode according to claim 5, wherein a lowest unoccupied molecular orbital (LUMO) level of the organic compound is substantially equal to or smaller than a highest occupied molecular orbital (HOMO) level of the first hole transporting layer.

10. The organic light emitting diode according to claim 5, wherein the hole injection layer further includes a host material, and an LUMO level of the organic compound is substantially equal to or smaller than a HOMO level of the host material.

11. The organic light emitting diode according to claim 5, further comprising:
a second emitting part between the first emitting part and the electron auxiliary layer and including a second hole transporting layer; and
a charge generation layer between the first and second emitting parts,
wherein the charge generation layer includes the organic compound.

12. An organic light emitting diode, comprising:
first and second electrodes facing each other;
a first emitting part between the first and second electrodes;
a second emitting part between the first emitting part and the second electrode and including a hole transporting layer; and
a charge generation layer between the first and second emitting parts,
wherein the charge generation layer includes an organic compound represented by the following Formula:

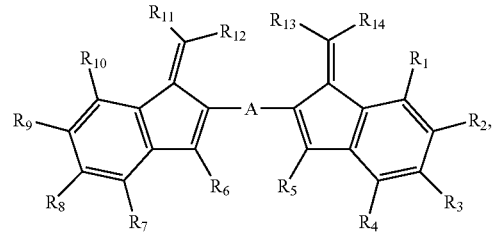

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group, fluorine, tri-fluoro methyl, tri-fluoro methoxy and trimethylsilyl, wherein at least one of $R_1$ to $R_{10}$ is the cyano group, and wherein at least one of $R_{11}$ to $R_{14}$ is the cyano group; and A is selected from substituted or non-substituted $C_6$ to $C_{30}$ aryl and substituted or non-substituted $C_3$ to $C_{30}$ heteroaryl.

13. The organic light emitting diode according to claim 12, wherein all of $R_{11}$ to $R_{14}$ are the cyano group.

14. The organic light emitting diode according to claim 12, wherein A is one of benzene, naphthalene, pyridine, diazine, dibenzofurane and dibenzothiophene.

15. The organic light emitting diode according to claim 12, wherein the organic compound is selected from:

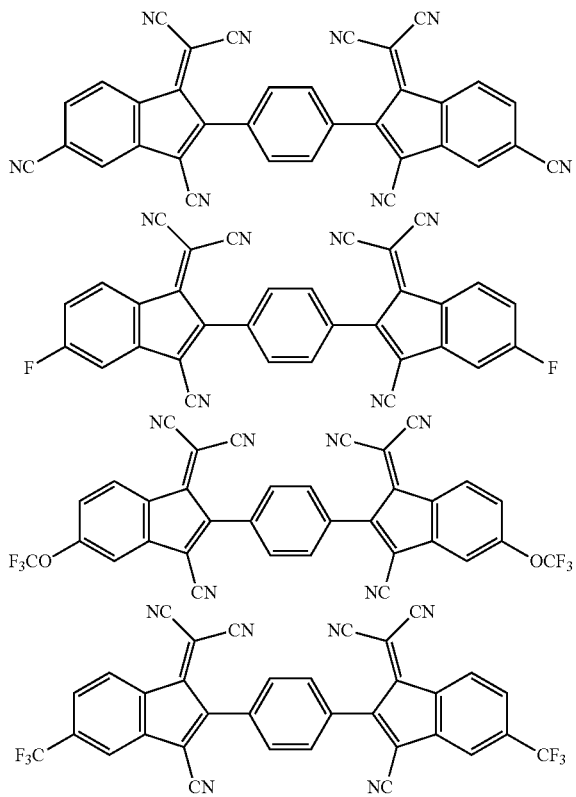

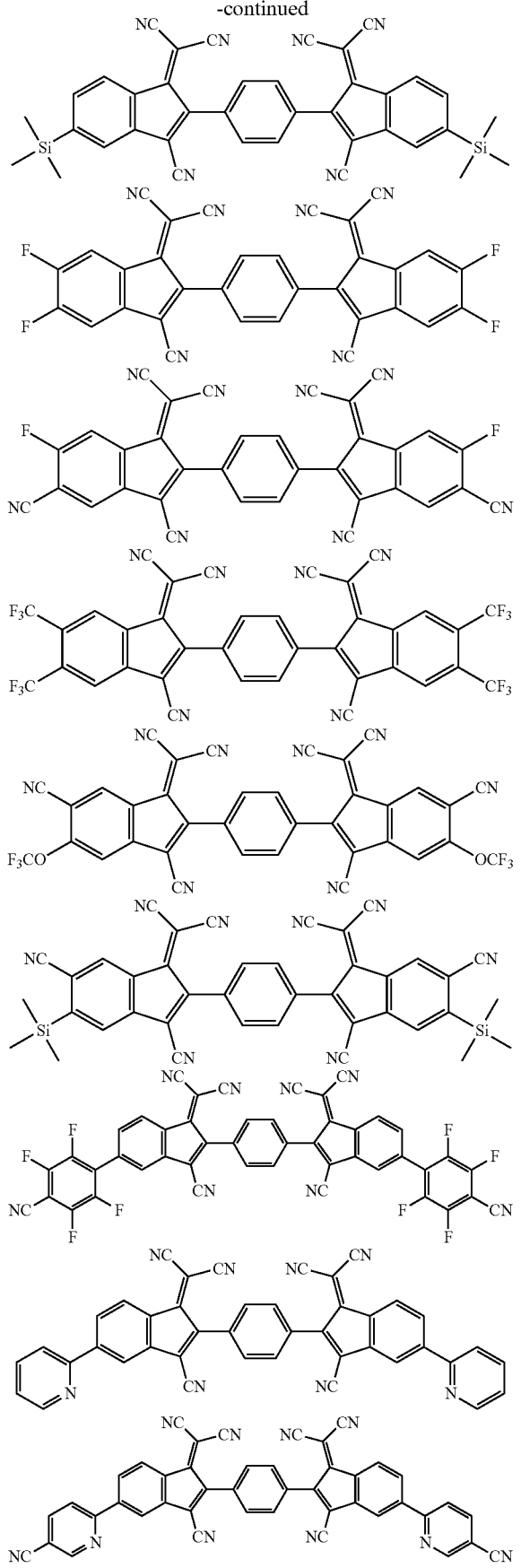
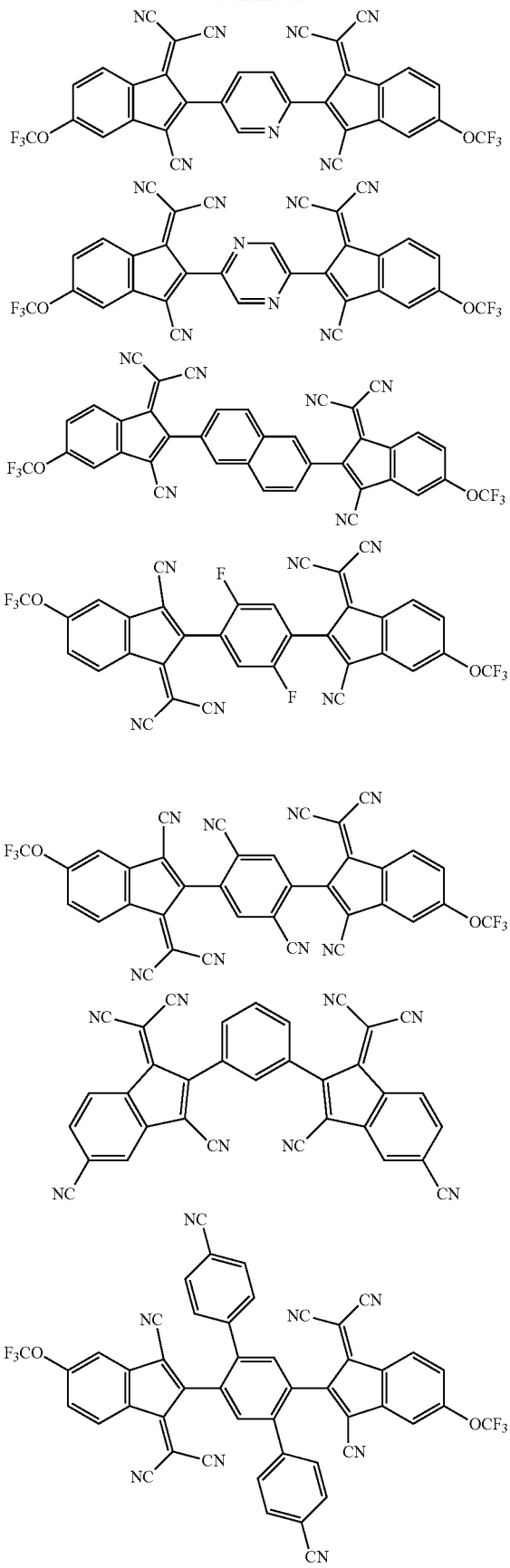

-continued
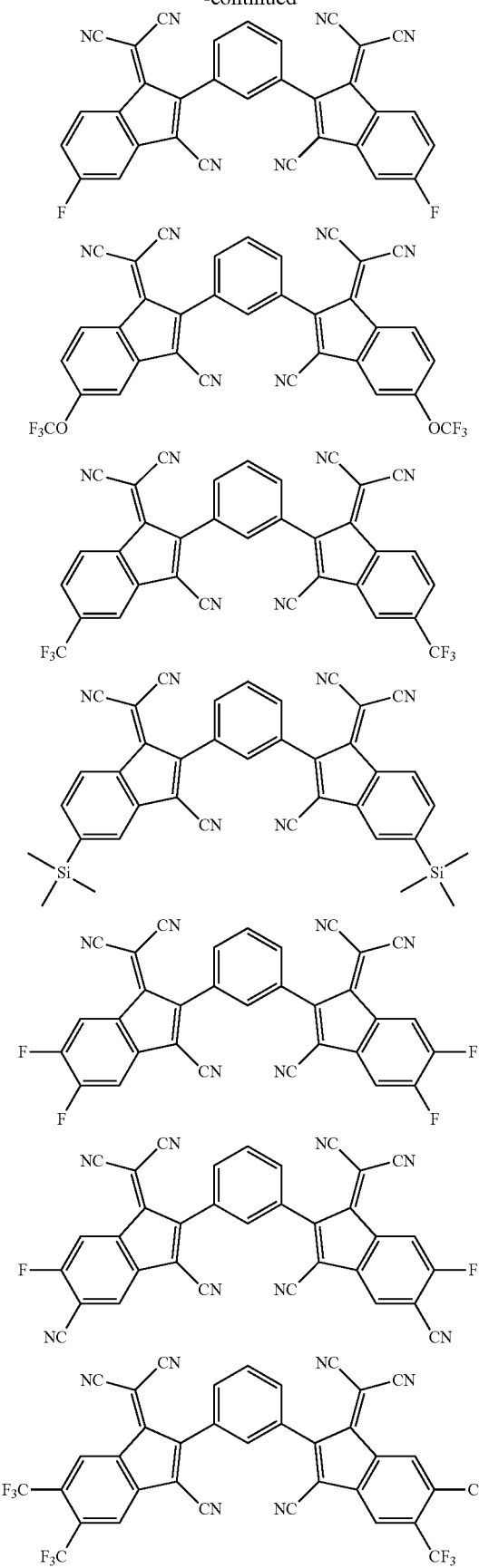
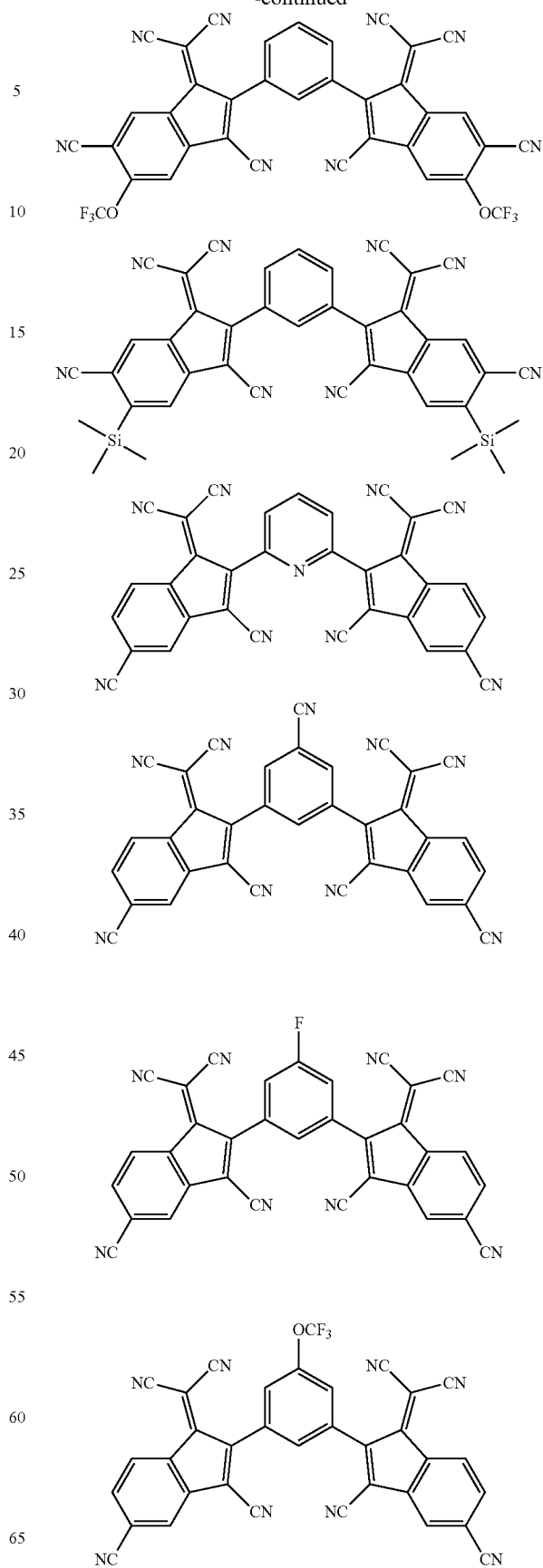

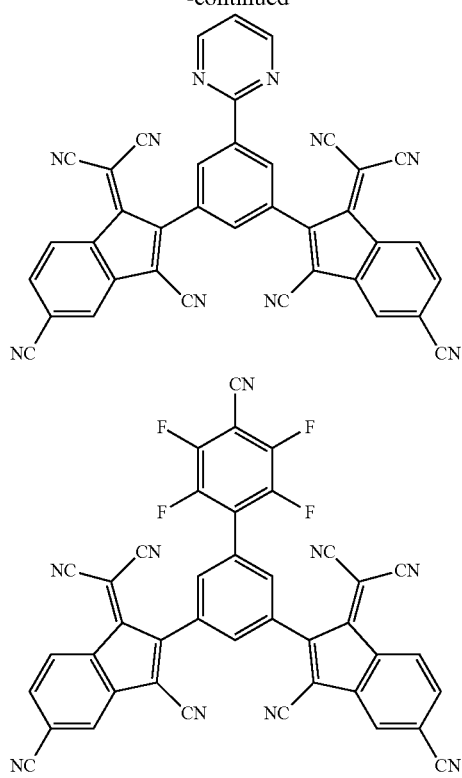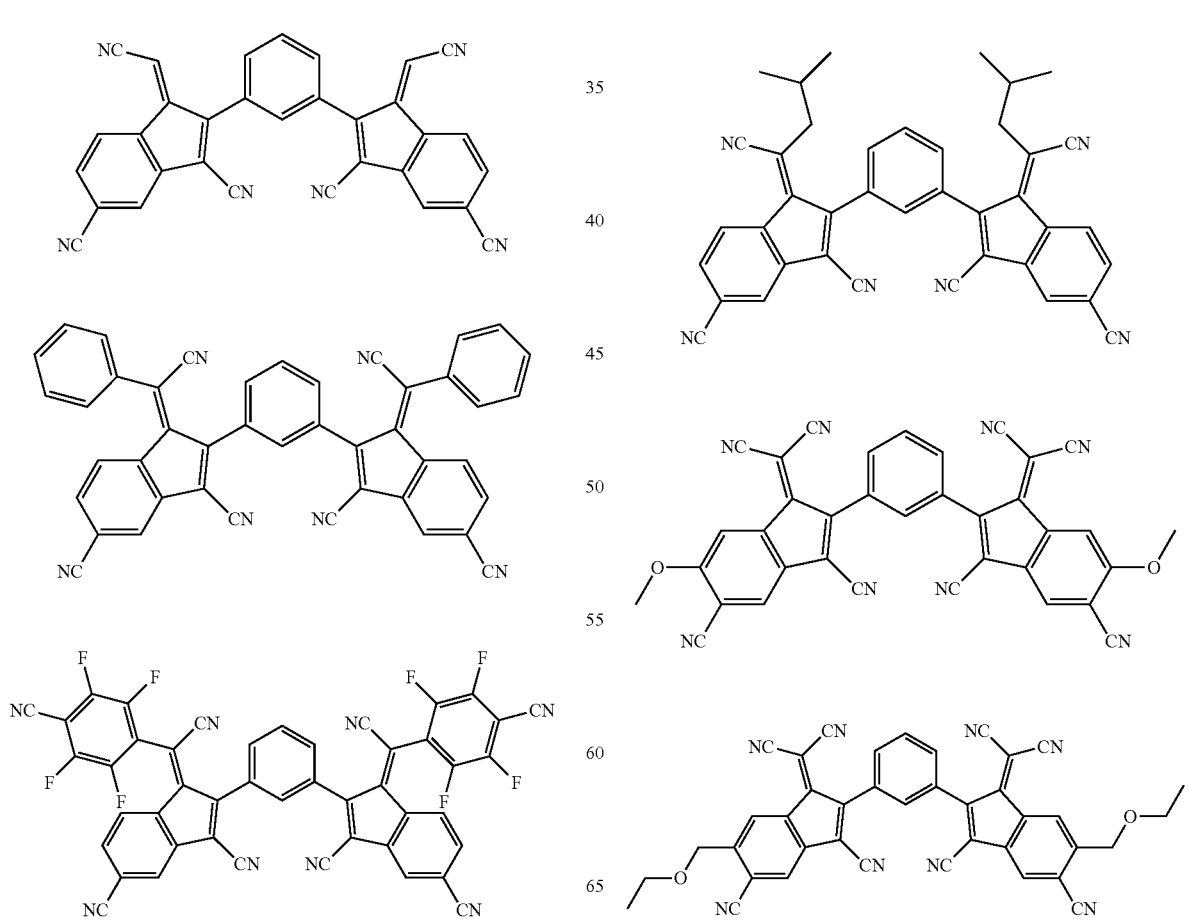

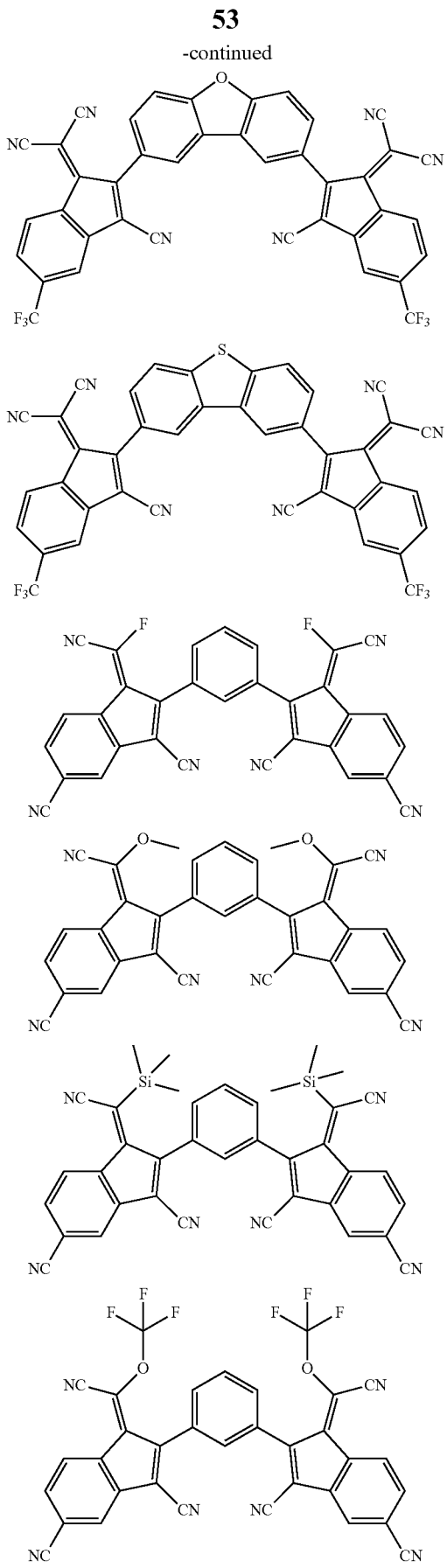

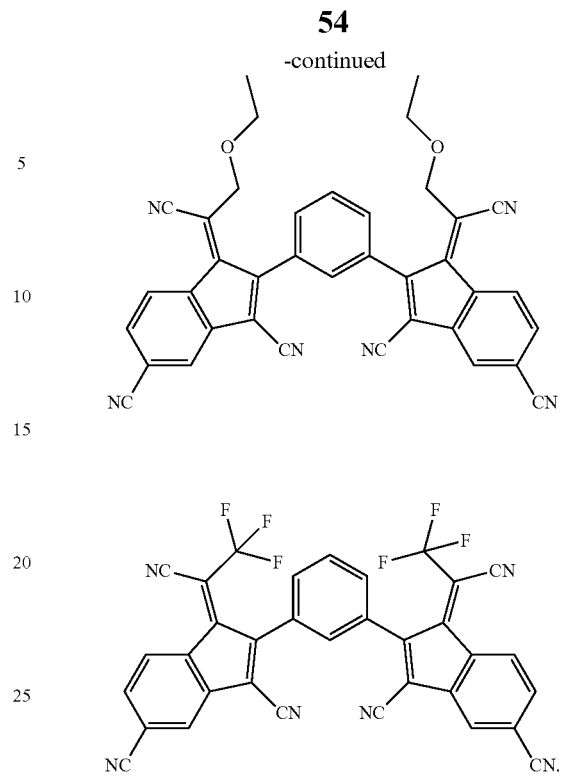

16. The organic light emitting diode according to claim 12, wherein an LUMO level of the organic compound is substantially equal to or smaller than a HOMO level of the hole transporting layer.

17. The organic light emitting diode according to claim 12, wherein the charge generation layer further includes a host material, and an LUMO level of the organic compound is substantially equal to or smaller than a HOMO level of the host material.

18. The organic light emitting diode according to claim 12, wherein the charge generation layer includes an N-type charge generation layer and a P-type charge generation layer between the N-type charge generation layer and the second emitting part, and wherein the P-type charge generation layer includes the organic compound.

19. An organic light emitting display device, comprising:
a substrate;
an organic light emitting diode over the substrate and including first and second electrodes facing each other, a first emitting part between the first and second electrodes and including a hole injection layer, a first hole transporting layer and a first emitting material layer and an electron auxiliary layer between the first emitting part and the second electrode; and
a thin film transistor between the substrate and the organic light emitting diode and connected to the organic light emitting diode,
wherein the first hole transporting layer includes an organic compound represented by the following Formula:

[Formula]

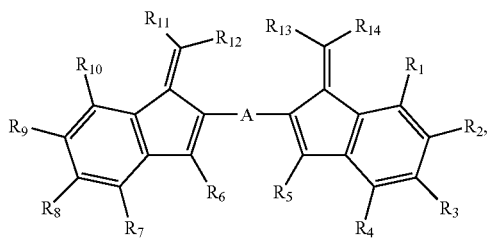

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group, fluorine, tri-fluoro methyl, tri-fluoro methoxy and trimethylsilyl, wherein at least one of $R_1$ to $R_{10}$ is the cyano group, wherein at least one of $R_{11}$ to $R_{14}$ is the cyano group; and A is selected from substituted or non-substituted $C_6$ to $C_{30}$ aryl and substituted or non-substituted $C_3$ to $C_{30}$ heteroaryl.

20. An organic light emitting display device, comprising:
a substrate;
an organic light emitting diode over the substrate and including first and second electrodes facing each other, a first emitting part between the first and second electrodes, a second emitting part between the first emitting part and the second electrode and including a hole transporting layer and a charge generation layer between the first and second emitting parts; and
a thin film transistor between the substrate and the organic light emitting diode and connected to the organic light emitting diode,
wherein the charge generation layer includes an organic compound represented by the following Formula:

[Formula]

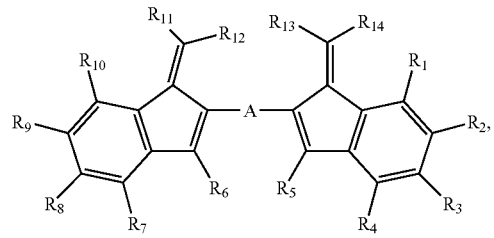

wherein each of $R_1$ to $R_{14}$ is independently selected from hydrogen, substituted or non-substituted $C_6$ to $C_{12}$ aryl, substituted or non-substituted $C_3$ to $C_{11}$ heteroaryl, substituted or non-substituted $C_1$ to $C_{10}$ alkyl, substituted or non-substituted $C_1$ to $C_{10}$ alkoxy, ether, cyano group, fluorine, tri-fluoro methyl, tri-fluoro methoxy and trimethylsilyl, wherein at least one of $R_1$ to $R_{10}$ is the cyano group, and wherein at least one of $R_{11}$ to $R_{14}$ is the cyano group; and A is selected from substituted or non-substituted $C_6$ to $C_{30}$ aryl and substituted or non-substituted $C_3$ to $C_{30}$ heteroaryl.

* * * * *